(12) United States Patent
Calilung et al.

(10) Patent No.: US 12,239,579 B2
(45) Date of Patent: Mar. 4, 2025

(54) HEADWORN SUPPORTS WITH PASSIVE VENTING AND REMOVABLE LENS

(71) Applicant: Oakley, Inc., Foothill Ranch, CA (US)

(72) Inventors: Ryan Anthony Calilung, Irvine, CA (US); Nathan Eino Heronen, Mission Viejo, CA (US); Steven G. Oldham, Corona, CA (US); Andrew Overton Wallace, Ladera Ranch, CA (US); Eric Yoshinari, Laguna Niguel, CA (US)

(73) Assignee: Oakley, Inc., Foothill Ranch, CA (US)

( * ) Notice: Subject to any disclaimer, the term of this patent is extended or adjusted under 35 U.S.C. 154(b) by 487 days.

(21) Appl. No.: 16/708,140

(22) Filed: Dec. 9, 2019

(65) Prior Publication Data

US 2020/0113738 A1 Apr. 16, 2020

Related U.S. Application Data

(63) Continuation of application No. 15/288,272, filed on Oct. 7, 2016, now Pat. No. 10,687,981.
(Continued)

(51) Int. Cl.
*A61F 9/02* (2006.01)
*G02C 3/02* (2006.01)
*G02C 11/08* (2006.01)

(52) U.S. Cl.
CPC .............. *A61F 9/028* (2013.01); *A61F 9/025* (2013.01); *A61F 9/026* (2013.01); *G02C 3/02* (2013.01);
(Continued)

(58) Field of Classification Search
CPC ....... G02C 2200/08; G02C 7/00; G02C 11/08
(Continued)

(56) References Cited

U.S. PATENT DOCUMENTS 245,268 A 8/1881 Andross
1,206,457 A 11/1916 Mills
(Continued)

FOREIGN PATENT DOCUMENTS

CN 201780416 3/2011
DE 102004058631 6/2006
(Continued)

OTHER PUBLICATIONS

"ESS Interchangeable Component Eyeshield (ICE) Tactical LE Safety Sunglasses 740-0007 Apparel Application: Performance, w/ Free Shipping." OpticsPlanet, May 18, 2013, https://www.opticsplanet.com/ess-ice-sunglasses-tactical.html (Year: 2013).*
(Continued)

*Primary Examiner* — Zachary W Wilkes
(74) *Attorney, Agent, or Firm* — Sterne, Kessler, Goldstein & Fox P.L.L.C.

(57) ABSTRACT

Provided herein are examples of bead worn supports, such as eyewear, configured to provide passive venting by providing pathways between a lens and a frame and/or by providing a smooth anterior profile to allow a laminar flow of air on an anterior surface of the lens. The pathways through the frame and lens of the eyewear can be configured such that they do not provide a direct path to the eye of a wearer. The headworn supports provided hemin can provide venting while reducing or preventing unwanted light, particles, or other debris from contacting the eye of the user. The headworn supports can also be configured to exhibit excellent ballistic performance.

33 Claims, 18 Drawing Sheets

Related U.S. Application Data

(60) Provisional application No. 62/239,740, filed on Oct. 9, 2015.

(52) U.S. Cl.
CPC .......... *G02C 11/08* (2013.01); *G02C 2200/08* (2013.01)

(58) Field of Classification Search
USPC .......................... 351/62, 90; 2/443, 436, 441
See application file for complete search history.

(56) References Cited

U.S. PATENT DOCUMENTS

| | | | |
|---|---|---|---|
| 1,308,477 A | 7/1919 | Blanchard |
| 1,588,775 A | 6/1926 | Schumacher |
| 1,839,386 A | 1/1932 | Fischer |
| 1,910,456 A | 5/1933 | Baker |
| 1,918,954 A | 7/1933 | Baker |
| 1,942,393 A | 1/1934 | Baker |
| 1,943,910 A | 1/1934 | Baker |
| 2,042,400 A | 5/1936 | Hon |
| 2,098,512 A | 11/1937 | Nerney |
| 2,391,361 A | 12/1945 | Stevenson |
| 2,443,422 A | 6/1948 | Hansen |
| 2,504,157 A | 4/1950 | Rosenheim |
| 2,652,746 A | 12/1950 | Shanks |
| 2,556,847 A | 6/1951 | Maclean |
| 2,610,323 A | 9/1952 | Johnson |
| 2,671,379 A | 3/1954 | Eloranta |
| 2,799,862 A | 7/1957 | Rowe |
| 2,571,704 A | 10/1961 | Gilden |
| 3,084,595 A | 4/1963 | Watts et al. |
| 3,214,767 A | 11/1965 | Weber |
| 3,229,303 A | 1/1966 | Jonassen |
| 3,233,250 A | 2/1966 | Jonassen |
| 3,383,707 A | 5/1968 | McNeill |
| 3,395,964 A | 8/1968 | Chartrice |
| 3,552,840 A | 1/1971 | Braget |
| 3,659,931 A | 5/1972 | Allen |
| 3,691,565 A | 9/1972 | Galonek |
| 3,826,564 A | 7/1974 | Werling, Sr. |
| 3,829,201 A | 8/1974 | Whiting |
| 3,901,589 A | 8/1975 | Bienenfeld |
| 3,931,646 A | 1/1976 | Loughner |
| 4,023,214 A | 5/1977 | Waldherr |
| 4,056,853 A | 11/1977 | Bottazzini et al. |
| 4,153,347 A | 5/1979 | Myer |
| 4,176,921 A | 12/1979 | Matthias |
| 4,178,080 A | 12/1979 | Elder |
| 4,264,987 A | 5/1981 | Runckel |
| 4,304,469 A | 12/1981 | Solomon |
| 4,314,814 A | 2/1982 | Deroode |
| 4,331,393 A | 5/1982 | Bradly, Jr. |
| 4,340,282 A | 7/1982 | Murakami |
| 4,357,080 A | 11/1982 | Solomon |
| 4,471,496 A | 9/1984 | Gardner, Jr. et al. |
| 4,515,448 A | 5/1985 | Tackles |
| 4,527,291 A | 7/1985 | Nussbickl |
| 4,616,367 A | 10/1986 | Jean et al. |
| 4,632,526 A | 12/1986 | Lhospice |
| 4,662,966 A | 5/1987 | Sumi et al. |
| 4,670,084 A | 6/1987 | Durand |
| 4,674,851 A | 6/1987 | Jannard |
| 4,686,712 A | 8/1987 | Spiva |
| 4,715,702 A | 12/1987 | Dillon |
| 4,730,915 A | 3/1988 | Jannard |
| 4,747,681 A | 5/1988 | Brower |
| 4,759,622 A | 7/1988 | Schmidthaler |
| 4,813,775 A | 3/1989 | Kaksonen |
| 4,822,158 A | 4/1989 | Porsche |
| 4,843,655 A | 7/1989 | Hegendorfer |
| 4,859,048 A | 8/1989 | Jannard |
| 4,867,550 A | 9/1989 | Jannard |
| 4,878,749 A | 11/1989 | McGee |
| 4,901,374 A | 2/1990 | Van der Woude |
| 4,951,322 A | 8/1990 | Lin |
| 4,978,209 A | 12/1990 | Ohba |
| 4,983,030 A | 1/1991 | Chandler |
| 5,007,727 A | 4/1991 | Kahaney et al. |
| 5,016,293 A | 5/1991 | Lickle |
| 5,048,944 A | 9/1991 | Porsche |
| 5,056,163 A | 10/1991 | Chou |
| 5,069,541 A | 12/1991 | Holmes et al. |
| 5,144,344 A | 9/1992 | Takahashi et al. |
| 5,170,502 A | 12/1992 | Hegendorfer et al. |
| 5,182,586 A | 1/1993 | Bennato |
| 5,182,587 A | 1/1993 | Hyoi |
| 5,191,364 A | 3/1993 | Kapfer |
| 5,208,614 A | 5/1993 | Jannard |
| 5,257,050 A | 10/1993 | Wiedner |
| 5,270,743 A | 12/1993 | Hofmair et al. |
| 5,291,230 A | 3/1994 | Bradley |
| 5,308,426 A | 5/1994 | Claveau |
| 5,357,292 A | 10/1994 | Wiedner |
| 5,359,370 A | 10/1994 | Mugnier |
| 5,373,331 A | 12/1994 | Vallalla et al. |
| 5,379,463 A | 1/1995 | Schleger et al. |
| 5,387,949 A | 2/1995 | Tackles |
| 5,390,369 A | 2/1995 | Tubin |
| 5,400,089 A | 3/1995 | Danloup et al. |
| 5,410,763 A | 5/1995 | Bolle |
| 5,412,438 A | 5/1995 | Bolle |
| 5,418,580 A | 5/1995 | Sondrol |
| 5,418,581 A | 5/1995 | Conway |
| 5,423,092 A | 6/1995 | Kawai |
| 5,428,407 A | 6/1995 | Sheffield |
| 5,455,639 A | 10/1995 | Magdelaine et al. |
| 5,467,148 A | 11/1995 | Conway |
| 5,493,348 A | 2/1996 | Harald, Jr. et al. |
| 5,536,828 A | 7/1996 | Deluca et al. |
| 5,541,674 A | 7/1996 | Jannard |
| 5,550,599 A | 8/1996 | Jannard |
| 5,576,775 A | 11/1996 | Bolle |
| 5,583,583 A | 12/1996 | Wilson |
| 5,587,747 A | 12/1996 | Bernheiser |
| 5,602,603 A | 2/1997 | Bondet |
| 5,608,470 A | 3/1997 | Sheffield |
| 5,610,668 A | 3/1997 | Mage |
| 5,617,588 A | 4/1997 | Canavan et al. |
| 5,619,287 A | 4/1997 | Tseng |
| 5,638,145 A | 6/1997 | Jannard et al. |
| 5,641,372 A | 6/1997 | Okuno |
| 5,648,832 A | 7/1997 | Houston et al. |
| 5,652,954 A | 8/1997 | Paiement et al. |
| 5,657,106 A | 8/1997 | Herald et al. |
| 5,685,022 A | 11/1997 | Essman et al. |
| 5,689,323 A | 11/1997 | Houston et al. |
| 5,708,489 A | 1/1998 | Jannard |
| 5,727,251 A | 3/1998 | Sherlock et al. |
| 5,752,280 A | 5/1998 | Hill |
| 5,760,866 A | 6/1998 | Wedeck et al. |
| 5,765,223 A | 6/1998 | McCausland |
| 5,768,716 A | 6/1998 | Porsche |
| 5,790,230 A | 8/1998 | Sved |
| 5,793,463 A | 8/1998 | Hirschman et al. |
| 5,796,461 A | 8/1998 | Stepan |
| 5,798,017 A | 8/1998 | Claveau |
| 5,802,622 A | 9/1998 | Baharad et al. |
| 5,805,261 A | 9/1998 | Houston et al. |
| 5,809,580 A | 9/1998 | Arnette |
| 5,815,235 A | 9/1998 | Runckel |
| 5,841,506 A | 11/1998 | Karasawa et al. |
| 5,862,529 A | 1/1999 | Moodie |
| 5,898,468 A | 4/1999 | Mage |
| 5,898,469 A | 4/1999 | Wang |
| 5,903,331 A | 5/1999 | Lin |
| 5,914,767 A | 6/1999 | Wedeck et al. |
| 5,929,963 A | 7/1999 | McNeal |
| 5,956,115 A | 9/1999 | Bolle |
| 5,956,116 A | 9/1999 | Ishiyama |
| 5,963,293 A | 10/1999 | Jannard |
| 5,969,789 A | 10/1999 | Houston et al. |
| 5,971,536 A | 10/1999 | Chiu |

(56) References Cited

U.S. PATENT DOCUMENTS

| | | |
|---|---|---|
| 5,971,538 A | 10/1999 | Heffner |
| 5,987,702 A | 11/1999 | Simioni |
| 6,007,199 A | 12/1999 | Yang |
| 6,009,564 A | 1/2000 | Tackles et al. |
| 6,010,217 A | 1/2000 | Houston et al. |
| 6,010,218 A | 1/2000 | Houston et al. |
| 6,047,410 A | 4/2000 | Dondero |
| 6,056,399 A | 5/2000 | Jannard et al. |
| 6,062,688 A | 5/2000 | Vinas |
| D428,620 S | 7/2000 | Maturaporn |
| 6,086,199 A | 7/2000 | Holland et al. |
| 6,094,751 A | 8/2000 | Parks |
| 6,098,204 A | 8/2000 | Arnette |
| 6,102,033 A | 8/2000 | Baribeau |
| 6,105,177 A | 8/2000 | Paulson et al. |
| 6,106,116 A | 8/2000 | Houston et al. |
| 6,119,279 A | 9/2000 | Haslbeck |
| 6,131,246 A | 10/2000 | Paulson et al. |
| 6,138,286 A | 10/2000 | Robrahn et al. |
| 6,168,271 B1 | 1/2001 | Houston et al. |
| 6,193,367 B1 | 2/2001 | Lee |
| 6,206,519 B1 | 3/2001 | Lin |
| 6,233,342 B1 | 3/2001 | Fernandez |
| 6,224,209 B1 | 5/2001 | Chen |
| 6,231,179 B1 | 5/2001 | Lee |
| 6,231,181 B1 | 5/2001 | Swab |
| 6,244,705 B1 | 6/2001 | Ledbetter et al. |
| 6,250,756 B1 | 6/2001 | Jannard |
| 6,260,964 B1 | 7/2001 | Kroman |
| 6,273,564 B1 | 8/2001 | Wedeck et al. |
| 6,276,794 B1 | 8/2001 | Chiang |
| 6,282,727 B1 | 9/2001 | Lindahl |
| 6,290,354 B1 | 9/2001 | Safran |
| 6,296,357 B1 | 10/2001 | Bof |
| D452,522 S | 12/2001 | Chiou |
| 6,349,422 B1 | 2/2002 | Schleger et al. |
| 6,357,873 B1 | 3/2002 | Spindelbalker |
| 6,375,321 B1 | 4/2002 | Lee et al. |
| 6,386,703 B1 | 5/2002 | Huang |
| 6,386,704 B1 | 5/2002 | Wu |
| 6,428,165 B1 | 8/2002 | Rivera |
| 6,464,353 B1 | 10/2002 | Spindelbalker |
| 6,474,812 B1 | 11/2002 | Moon |
| 6,477,717 B1 | 11/2002 | Winefordner et al. |
| 6,502,937 B2 | 1/2003 | Yang |
| 6,533,412 B1 | 3/2003 | Wang et al. |
| 6,540,351 B1 | 4/2003 | Meiler |
| 6,543,895 B2 | 4/2003 | Fukai |
| 6,550,912 B2 | 4/2003 | Vitaloni |
| 6,550,914 B1 | 4/2003 | Kapfer |
| 6,561,647 B1 | 5/2003 | Chen |
| 6,564,804 B2 | 5/2003 | Salatka et al. |
| 6,575,570 B2 | 6/2003 | Mauri |
| 6,637,877 B1 | 10/2003 | Hartley et al. |
| 6,641,263 B2 | 11/2003 | Olney |
| D485,570 S | 1/2004 | Teng |
| 6,702,439 B1 | 3/2004 | Lee |
| 6,712,465 B1 | 3/2004 | Teng |
| 6,715,157 B2 | 4/2004 | Mage |
| 6,718,561 B2 | 4/2004 | Dondero |
| 6,732,383 B2 | 5/2004 | Cleary et al. |
| 6,742,890 B1 | 6/2004 | Teng |
| 6,742,891 B2 | 6/2004 | Chen |
| 6,749,299 B1 | 6/2004 | Hsu |
| 6,783,235 B1 | 8/2004 | Lin |
| 6,786,592 B2 | 9/2004 | Rivera |
| 6,793,336 B2 | 9/2004 | Min |
| 6,804,835 B2 | 10/2004 | Chou |
| 6,817,709 B2 | 11/2004 | Min |
| 6,834,951 B2 | 12/2004 | Xie |
| 6,854,845 B1 | 2/2005 | Goldman et al. |
| 6,857,738 B1 | 2/2005 | Bove et al. |
| 6,863,394 B1 | 3/2005 | Nelson et al. |
| 6,863,395 B1 | 3/2005 | Teng |
| 6,877,169 B2 | 4/2005 | Acquaviva |
| 6,908,193 B2 | 6/2005 | Cyr |
| D508,255 S | 8/2005 | Wu |
| 6,923,537 B2 | 8/2005 | Hartley et al. |
| 6,926,403 B2 | 8/2005 | Yi et al. |
| 6,926,404 B2 | 8/2005 | Bassahon et al. |
| 6,928,663 B1 | 8/2005 | Tappeiner |
| 6,929,364 B1 | 8/2005 | Jannard |
| 6,938,277 B2 | 9/2005 | Lindahl |
| 6,942,338 B2 | 9/2005 | Ku |
| 6,948,813 B2 | 9/2005 | Parks |
| 6,953,247 B1 | 10/2005 | Duffy et al. |
| D511,540 S | 11/2005 | Hsu |
| 6,959,988 B1 | 11/2005 | Sheldon |
| 6,964,067 B1 | 11/2005 | Hartman |
| 6,964,477 B1 | 11/2005 | Teng |
| 6,969,170 B1 | 11/2005 | Smith |
| 6,969,171 B2 | 11/2005 | Lane et al. |
| D513,033 S | 12/2005 | Hsu |
| 6,991,333 B2 * | 1/2006 | Van Atta .................. G02C 5/12 351/103 |
| 6,994,434 B2 | 2/2006 | Blanchette et al. |
| 7,000,263 B2 | 2/2006 | McNeal |
| 7,003,802 B2 | 2/2006 | Broersma |
| 7,029,114 B2 | 4/2006 | Smith |
| 7,036,152 B2 | 5/2006 | Gafforio et al. |
| 7,036,927 B2 | 5/2006 | Kapfer |
| 7,039,959 B2 | 5/2006 | Dondero |
| 7,058,991 B2 | 6/2006 | Hartman |
| 7,083,276 B2 | 8/2006 | Olney |
| 7,090,346 B2 | 8/2006 | Tsai |
| 7,091,634 B2 | 8/2006 | Yi et al. |
| 7,100,215 B2 | 9/2006 | Shiue |
| 7,137,426 B2 | 11/2006 | Neri et al. |
| 7,137,700 B2 | 11/2006 | DiChiara et al. |
| 7,150,525 B2 | 12/2006 | Yang |
| 7,163,289 B2 | 1/2007 | Wedeck et al. |
| D537,097 S | 2/2007 | Freeman |
| D537,860 S | 3/2007 | Freeman |
| 7,192,134 B2 | 3/2007 | Teng |
| 7,200,875 B2 | 4/2007 | Dondero |
| 7,204,589 B2 | 4/2007 | Pieterman |
| 7,219,992 B1 | 5/2007 | Wu |
| 7,219,993 B1 | 5/2007 | Chiou |
| 7,222,958 B1 | 5/2007 | Chiou |
| 7,222,959 B2 | 5/2007 | Jannard |
| 7,234,808 B2 | 6/2007 | Bruck |
| 7,237,891 B2 | 7/2007 | Min |
| 7,241,007 B2 | 7/2007 | Cody |
| 7,244,022 B2 | 7/2007 | Lee |
| 7,261,410 B1 | 8/2007 | Chen |
| 7,267,434 B2 | 9/2007 | Lane et al. |
| 7,267,737 B2 | 9/2007 | Neri et al. |
| 7,278,733 B2 | 10/2007 | Olney |
| 7,296,887 B1 | 11/2007 | Hsiung |
| 7,328,999 B2 | 2/2008 | Zelman |
| 7,343,631 B2 | 3/2008 | Lin |
| 7,347,545 B1 | 3/2008 | Jannard et al. |
| 7,364,287 B2 | 4/2008 | Lee et al. |
| 7,370,961 B2 | 5/2008 | Lerner et al. |
| 7,384,141 B2 | 6/2008 | Zelman |
| 7,390,086 B2 | 6/2008 | Lee |
| 7,396,124 B1 | 7/2008 | Wang |
| 7,407,281 B2 | 8/2008 | Tagawa |
| 7,425,065 B2 | 9/2008 | Wang |
| 7,431,453 B2 | 10/2008 | Hogan |
| 7,434,929 B2 | 10/2008 | Jackson |
| 7,441,889 B2 | 10/2008 | Zelman |
| 7,452,068 B2 | 11/2008 | Collier et al. |
| 7,452,069 B2 | 11/2008 | Lipawsky |
| 7,478,906 B2 | 1/2009 | Fielding |
| 7,481,529 B1 | 1/2009 | Chen |
| 7,497,569 B2 | 3/2009 | Webb |
| 7,520,217 B2 | 4/2009 | Roberts et al. |
| 7,520,604 B2 | 4/2009 | Choi |
| 7,520,605 B1 | 4/2009 | Chen |
| 7,526,813 B2 | 5/2009 | Tominaga et al. |
| 7,553,013 B2 | 6/2009 | Tsai |
| 7,556,373 B2 | 7/2009 | VanAtta et al. |
| 7,563,341 B2 | 7/2009 | Ferguson et al. |

(56) References Cited

U.S. PATENT DOCUMENTS

| | | |
|---|---|---|
| 7,585,072 B1 | 9/2009 | Wang-Lee |
| 7,585,073 B2 | 9/2009 | Paolino |
| 7,594,280 B2 | 9/2009 | Lindahl |
| 7,594,723 B2 | 9/2009 | Jannard et al. |
| 7,604,346 B2 | 10/2009 | Wang |
| 7,648,233 B2 | 1/2010 | Blanshay et al. |
| 7,658,492 B2 | 2/2010 | Siu |
| 7,681,257 B1 | 3/2010 | Broersma |
| 7,686,449 B2 | 3/2010 | Jannard et al. |
| 7,703,913 B2 | 4/2010 | Huang |
| D615,580 S | 5/2010 | Baden et al. |
| D616,485 S | 5/2010 | Thixton |
| 7,712,894 B2 | 5/2010 | Tsai |
| 7,712,896 B1 | 5/2010 | Lee |
| 7,725,959 B2 | 6/2010 | Wang-Lee |
| D622,303 S | 8/2010 | Thixton |
| D622,304 S | 8/2010 | Baden et al. |
| 7,771,043 B2 | 8/2010 | Welchel et al. |
| 7,780,810 B2 | 8/2010 | Hamano |
| 7,810,174 B2 | 10/2010 | Matera |
| D629,035 S | 12/2010 | Moritz |
| 7,850,301 B2 | 12/2010 | DiChiara |
| 7,856,673 B2 | 12/2010 | Reed |
| 7,887,181 B1 | 2/2011 | Chen |
| 7,908,668 B2 | 3/2011 | Folkesson |
| D639,845 S | 6/2011 | Fuchs |
| D640,725 S | 6/2011 | Moritz et al. |
| D640,727 S | 6/2011 | Moritz et al. |
| 7,954,942 B2 | 6/2011 | Calilung et al. |
| D646,708 S | 10/2011 | Baden et al. |
| 8,028,350 B2 | 10/2011 | Hogen |
| D649,178 S | 11/2011 | Moritz |
| D653,697 S | 2/2012 | Taylor |
| D653,698 S | 2/2012 | Taylor |
| D659,180 S | 5/2012 | Moritz |
| 8,192,015 B2 | 6/2012 | Taylor et al. |
| 8,235,523 B2 | 8/2012 | Yang |
| 8,307,466 B2 | 11/2012 | Hsu |
| 8,316,470 B2 | 11/2012 | McNeal et al. |
| D675,666 S | 2/2013 | Thixton et al. |
| 8,408,695 B2 | 4/2013 | Calilung et al. |
| 8,414,119 B2 | 4/2013 | Yeh |
| 8,424,474 B2 | 4/2013 | Berns |
| 8,469,510 B2 * | 6/2013 | Belbey ............... A61F 9/027 351/86 |
| 8,534,830 B2 | 9/2013 | Taylor et al. |
| 8,661,562 B2 | 3/2014 | Calilung et al. |
| 8,668,330 B2 | 3/2014 | Reyes et al. |
| 8,746,877 B2 | 6/2014 | Belbey et al. |
| 8,800,067 B2 | 8/2014 | Saylor et al. |
| 8,850,626 B2 | 10/2014 | Reyes et al. |
| 8,881,316 B2 | 11/2014 | Reyes et al. |
| 8,911,076 B2 | 12/2014 | Calilung et al. |
| 9,016,855 B2 * | 4/2015 | Chen .................. G02C 5/10 351/149 |
| 9,122,078 B2 | 9/2015 | Calilung et al. |
| 9,188,792 B2 | 11/2015 | Calilung et al. |
| 9,192,520 B2 | 11/2015 | Cater et al. |
| 9,241,833 B2 | 1/2016 | Cater et al. |
| 9,256,080 B2 * | 2/2016 | Earley ................ G02C 7/02 |
| 9,261,711 B1 * | 2/2016 | Chen .................. G02C 1/04 |
| 9,279,999 B1 * | 3/2016 | Weng ................. G02C 5/2209 |
| 9,463,117 B2 | 10/2016 | Belbey et al. |
| 9,561,684 B2 * | 2/2017 | Rivera, III ........... A61F 9/023 |
| 9,709,817 B2 | 7/2017 | Calilung et al. |
| 9,717,631 B2 | 8/2017 | Cater et al. |
| 9,833,032 B2 * | 12/2017 | Jacobsen ............. A42B 3/147 |
| 2003/0048405 A1 | 3/2003 | Rivera |
| 2003/0067584 A1 | 4/2003 | Siu |
| 2003/0188376 A1 | 10/2003 | Dondero |
| 2004/0025232 A1 * | 2/2004 | Hartley ............... A61F 9/025 2/452 |
| 2004/0083540 A1 | 5/2004 | Dondero |
| 2004/0139532 A1 | 7/2004 | Parks |
| 2004/0141146 A1 | 7/2004 | Blanchette et al. |
| 2004/0141147 A1 | 7/2004 | Cyr |
| 2004/0160570 A1 | 8/2004 | Polovin |
| 2005/0070434 A1 | 3/2005 | Drake |
| 2005/0105041 A1 | 5/2005 | Lerner et al. |
| 2005/0132478 A1 | 6/2005 | Canavan |
| 2005/0160521 A1 | 7/2005 | Hussey |
| 2005/0268385 A1 | 12/2005 | Hartman et al. |
| 2005/0270477 A1 | 12/2005 | Curci et al. |
| 2005/0286013 A1 | 12/2005 | Aylor |
| 2006/0048289 A1 | 3/2006 | Shiue |
| 2006/0119790 A1 | 6/2006 | Tsai |
| 2006/0179554 A1 | 8/2006 | Barton |
| 2006/0191062 A1 | 8/2006 | Matera |
| 2006/0238700 A1 | 10/2006 | Del Vecchio |
| 2006/0250571 A1 | 11/2006 | Li |
| 2006/0256281 A1 | 11/2006 | Li |
| 2006/0283555 A1 | 12/2006 | Green |
| 2007/0006425 A1 | 1/2007 | Woodbury |
| 2007/0024806 A1 | 2/2007 | Blanshay |
| 2007/0033718 A1 | 2/2007 | Lin |
| 2007/0091253 A1 | 4/2007 | Chao |
| 2007/0109490 A1 | 5/2007 | Collier et al. |
| 2007/0121059 A1 | 5/2007 | Chiou |
| 2007/0153230 A1 | 7/2007 | Musal et al. |
| 2007/0182916 A1 | 8/2007 | Blanshay et al. |
| 2007/0240812 A1 | 10/2007 | Bortolato |
| 2007/0261782 A1 | 11/2007 | Frye et al. |
| 2008/036961 A1 | 2/2008 | Zhou |
| 2008/0072365 A1 | 3/2008 | Alberto |
| 2008/0094567 A1 | 4/2008 | Choi |
| 2008/0129952 A1 * | 6/2008 | Jannard ............... G02C 5/124 351/105 |
| 2008/0137028 A1 | 6/2008 | Webb |
| 2008/0155736 A1 | 7/2008 | Paulson et al. |
| 2008/0198323 A1 | 8/2008 | Yu |
| 2008/0266515 A1 | 10/2008 | Hou |
| 2008/0301858 A1 | 12/2008 | Wang-Lee |
| 2008/0304005 A1 | 12/2008 | DiChiara |
| 2009/0007388 A1 | 1/2009 | Villeneuva |
| 2009/0015784 A1 | 1/2009 | Van Atta |
| 2009/0019620 A1 | 1/2009 | Reed |
| 2009/0038057 A1 | 2/2009 | Tews |
| 2009/0038059 A1 | 2/2009 | McNeal et al. |
| 2009/0044317 A1 | 2/2009 | Tews |
| 2009/0066906 A1 | 3/2009 | Huang |
| 2009/0079931 A1 | 3/2009 | Yang |
| 2009/0122254 A1 | 5/2009 | Van Der Heijde et al. |
| 2009/0151037 A1 | 6/2009 | Hsu |
| 2009/0217444 A1 | 9/2009 | Pan |
| 2009/0225271 A1 | 9/2009 | Radmard et al. |
| 2009/0300830 A1 | 12/2009 | Mage |
| 2009/0313746 A1 | 12/2009 | Wang |
| 2009/0323015 A1 | 12/2009 | Siu |
| 2010/0186153 A1 | 7/2010 | Reyes et al. |
| 2010/0201937 A1 | 8/2010 | Gardaz |
| 2010/0231849 A1 | 9/2010 | Maria Barlag et al. |
| 2010/0231850 A1 | 9/2010 | Hones |
| 2011/0001921 A1 * | 1/2011 | Matera ................ G02C 11/08 351/62 |
| 2011/0170049 A1 | 7/2011 | Chen |
| 2011/0194065 A1 | 8/2011 | Belbey et al. |
| 2011/0242479 A1 | 10/2011 | Radmard et al. |
| 2011/0258758 A1 | 10/2011 | Renaud |
| 2011/0279771 A1 | 11/2011 | Chen |
| 2012/0127421 A1 | 5/2012 | Li |
| 2012/0218507 A1 * | 8/2012 | Calilung ............. G02C 11/08 351/140 |
| 2012/0255104 A1 | 10/2012 | Didier |
| 2012/0257159 A1 | 10/2012 | Silver |
| 2012/0308743 A1 * | 12/2012 | Rivera, III .......... A61F 9/023 428/29 |
| 2013/0019374 A1 | 1/2013 | Schwartz |
| 2013/0083285 A1 | 4/2013 | McNeal et al. |
| 2013/0104300 A1 | 5/2013 | Park |
| 2014/0043682 A1 * | 2/2014 | Hussey ............... G02C 5/02 359/466 |
| 2014/0059747 A1 | 3/2014 | Belbey et al. |
| 2014/0063437 A1 | 3/2014 | Cater et al. |
| 2014/0063438 A1 | 3/2014 | Cater et al. |

(56) References Cited

U.S. PATENT DOCUMENTS

| | | | |
|---|---|---|---|
| 2014/0078460 | A1 | 3/2014 | Chang et al. |
| 2014/0218677 | A1* | 8/2014 | Chen ............ G02C 1/04 351/140 |
| 2016/0216533 | A1 | 7/2016 | Calilung et al. |
| 2017/0095371 | A1 | 4/2017 | Cater et al. |
| 2017/0160562 | A1 | 6/2017 | McCabe et al. |
| 2017/0160563 | A1 | 6/2017 | Calilung et al. |

FOREIGN PATENT DOCUMENTS

| | | |
|---|---|---|
| EP | 0 496 292 | 1/1991 |
| EP | 0 495 767 | 7/1992 |
| EP | 0 702 803 | 3/1996 |
| EP | 1382989 | 1/2004 |
| EP | 1428061 | 6/2004 |
| EP | 1 810 648 | 7/2007 |
| EP | 1 830 221 | 9/2007 |
| EP | 2 042 910 | 4/2009 |
| EP | 2 090 921 | 8/2009 |
| FR | 1 126 329 | 11/1956 |
| FR | 1290346 A | 4/1962 |
| FR | 2 088 866 | 1/1972 |
| FR | 2 626 682 | 8/1989 |
| FR | 2 684 292 | 6/1993 |
| FR | 2 800 173 | 4/2001 |
| GB | 468443 | 7/1937 |
| GB | 512419 | 9/1939 |
| GB | 2181859 | 4/1987 |
| GB | 2199155 | 6/1988 |
| GB | 2278459 | 11/1994 |
| JP | 62-3774 Y2 | 7/1926 |
| JP | 56-126611 | 2/1955 |
| JP | 56-066915 | 6/1981 |
| JP | 57-176119 | 11/1982 |
| JP | 59-79827 | 5/1984 |
| JP | 59-104127 | 6/1984 |
| JP | 60-094624 | 6/1985 |
| JP | 60-146218 | 8/1985 |
| JP | 60-143420 | 9/1985 |
| JP | 61-160422 | 10/1986 |
| JP | 219021 | 2/1990 |
| JP | 02-240360 | 9/1990 |
| JP | 07-032628 | 2/1995 |
| JP | 07-64028 | 3/1995 |
| JP | 07-140423 | 6/1995 |
| JP | 7-234385 | 9/1995 |
| JP | 3021121 U | 2/1996 |
| JP | 08-062544 | 3/1996 |
| JP | 10-239642 | 9/1998 |
| JP | 2002-228986 | 8/2002 |
| JP | 2002-540895 A | 12/2002 |
| JP | 2003-536093 | 12/2003 |
| JP | 2005-067551 | 3/2005 |
| JP | 2009-139921 | 6/2009 |
| JP | 2010-224130 | 10/2010 |
| JP | 2012-509497 | 4/2012 |
| KR | 10-2014-0027745 | 3/2014 |
| WO | WO 94/29763 | 12/1994 |
| WO | WO 97/21135 | 6/1997 |
| WO | WO 97/41815 | 11/1997 |
| WO | WO 99/64918 | 12/1999 |
| WO | WO 03/023495 | 3/2003 |
| WO | WO 2005/119343 | 12/2005 |
| WO | WO 2007/049070 | 5/2007 |
| WO | WO 2008/125743 | 10/2008 |
| WO | WO 2010/021419 | 2/2010 |
| WO | WO 2011/117909 | 9/2011 |
| WO | WO 2013/154582 | 10/2013 |
| WO | WO 2014/124352 | 8/2014 |
| WO | WO 2015/148770 | 10/2015 |

OTHER PUBLICATIONS

"XSG Ballistic Goggle Kit with Interchangeable Lenses: Gray, Amber, Clear." Blasters Tool & Supply Co., Inc, Dec. 22, 2010, https://www.blasterstool.com/ballisticgogglekitwithinterchangablelenses.aspx. (Year: 2010).*
Partial International Search Report in PCT/US2016/056065, dated Jan. 20, 2017.
Invitation to Pay Additional Fees in PCT/US2016/056065, dated Jan. 20, 2017; 9 pages.
Search Report and Written Opinion in PCT/US2016/056065, dated Mar. 16, 2017; 24 pages.
Pivlock V2—Smith Optics Elite, dated Nov. 7, 2013, available at: https://www.youtube.com/watch?v=WIVQVm01xOg.
Oakley Wind Jacket, released at least as early as Aug. 30, 2011.
Japanese Search Report from related Japanese Patent Application No. 2018-518503 with English-language Translation Attached, issued Jun. 25, 2019; 75 pages.

* cited by examiner

HEADWORN SUPPORTS WITH PASSIVE VENTING AND REMOVABLE LENS

CROSS-REFERENCE TO RELATED APPLICATIONS

This application is a continuation application of U.S. patent application Ser. No. 15/288,272 filed on Oct. 7, 2016 titled HEADWORN SUPPORTS WITH PASSIVE VENTING AND REMOVABLE LENS, which claims priority to U.S. Provisional App. No. 62/239,740 filed Oct. 9, 2015, titled EYEWEAR WITH PASSIVE VENTING AND REMOVABLE LENS. The foregoing applications are incorporated herein by reference in their entirety and are to be considered a part of this specification.

BACKGROUND

Field

Some embodiments of this disclosure relate to passively vented headworn supports, and more specifically to headworn supports, such as eyewear, having a frame and a lens configured to allow for efficient ventilation of the lens; and some embodiments relate to head wont supports, such as eyewear, with one or more removable lenses, and more specifically to headworn supports, such as eyewear, with a removable lens that can be installed in headworn supports having different structures and/or functions including, but not limited to, eyeglasses and goggles.

Description of Related Art

A wide variety of eyewear products are available with various drawbacks, such as insufficient ventilation (which can lead to wearer discomfort and visual impairment), insufficient protection (e.g., at lateral portions of the eyewear), and insufficient ballistic impact resistance, among other deficiencies.

SUMMARY

Example embodiments described herein have several features, no single one of which is indispensable or solely responsible for their desirable attributes. Without limiting the scope of the claims, some of the advantageous features will now be summarized. While the features and structures are described below in connection with embodiments of eyewear such as eyeglasses and goggles, it is to be understood that the features and structures can be implemented in any headworn support (i.e., a headworn article that can support one or more lenses in the wearer's field of view). For example, other headworn supports can include, but are not limited to, helmets, face masks, balaclavas, and breaching shields.

In a first aspect, an eyewear is provided that includes a lens having a posterior surface adjacent a face of a user when worn and an anterior surface opposite the posterior surface. The eyewear includes a frame comprising a plurality of contact points configured to contact the lens. The eyewear includes at least one earstem attached to the frame. The eyewear includes a retention assembly attached to the frame and the at least one earstem, the retention assembly configured to secure the lens to the frame so that the lens contacts the frame at the plurality of contact points. When the lens is secured in the eyewear, an upper edge of the lens and a lower edge of the frame are spaced apart between contact points to allow venting of the lens and a total length of the upper edge that is spaced apart from the frame is at least 20% of the total chord length of the upper edge of the lens. A posterior surface of the lens between contact points extends a protrusion distance beyond a posterior extension of the posterior surface of the lens, wherein the protrusion distance is less than or equal to about 4 mm.

In some embodiments of the first aspect, one or more of the contact points comprises an attachment point configured to structurally support the lens when the lens is secured in the eyewear. In some embodiments of the first aspect, the total, continuous length of the upper edge that is spaced apart from the frame is at least 50% of the total chord length of the upper edge of the lens. In a further embodiment, the total length of the upper edge that is spaced apart from the frame is less than or equal to 80% of the total chord length of the upper edge of the lens.

In some embodiments of the first aspect, the protrusion distance is less than or equal to 0. In some embodiments of the first aspect, the protrusion distance is less than or equal to 3.2 limes a center thickness of the lens. In some embodiments of the first aspect, when worn, there is no direct path from an eye of the user between the upper edge of the lens and the lower edge of the frame. In some embodiments of the first aspect, the posterior extension docs not intersect the frame over at least half of the total length of the upper edge of the lens. In some embodiments of the first aspect, when worn, a viewing angle from an eye of a user to an edge of the frame is greater than or equal to about 48 degrees. In some embodiments of the first aspect, a venting angle is greater titan 0 degrees above the horizon.

In some embodiments of the first aspect, the eyewear is configured to withstand a ballistic impact of a 0.25" ball having a speed of al least about 150 ft/s. In some embodiments of the first aspect, the eyewear is configured to withstand a ballistic impact of a .15 caliber cylindrical-shaped, chamfered-edge fragment having a speed of at least about 640 ft/s. In some embodiments of the first aspect, a lower edge of the lens does not contact the frame.

In some embodiments of the first aspect, the lens is configured to be secured in a goggle in addition to the eyewear, the goggle including a lens support adapted to support the lens in a wearer's field of view, the lens support having a channel configured to receive the lens and secure the lens in place; and a padded layer attached to an anterior surface of the lens support, the padded layer configured to be pressed against a head of the wearer when in use.

In a second aspect, an eyewear is provided that includes a lens, a frame comprising one or more contact points configured to contact the lens, the frame configured to position the lens in a line of sight of a wearer, and an earstem hingedly attached to the frame. The eyewear also includes a retention assembly attached to the frame and the earstem, the retention assembly configured to secure the lens to the frame so that the lens contacts the frame at the plurality of contact points. When the lens is secured in the eyewear, an upper edge of the lens and a lower edge of the frame are spaced apart between contact points to allow venting of the lens. A venting angle formed by an anterior surface of the frame and the upper edge of the lens is greater than or equal to 0 so that gaps between the upper edge of the lens and the lower edge of the frame between contact points are not visible when the eyewear is viewed straight on.

In some embodiments of the second aspect, the retention assembly comprises a door configured to be actuatable independent of the at least one earstem when the at least one earstem is folded behind the frame. In a further embodiment, the retention assembly further comprises a protrusion configured to be inserted through a locking receptacle in the retention assembly when the retention assembly secures the lens to the frame. In a further embodiment, the door of the retention assembly is configured to transition from open to closed to secure the lens to the frame when the earstem transitions from a folded position behind the frame to an extended position.

In some embodiments of the second aspect, the eyewear further includes at least two attachment points configured to attach to opposite, lateral edges of the lens. In some embodiments of the second aspect, the eyewear further includes an attachment point at a midpoint of the frame. In some embodiments of the second aspect, the eyewear further includes an attachment point comprising an opening formed between two side walls formed by the frame.

In a third aspect, tin eyewear kit is provided that includes a lens. The kit also includes an eyeglass frame that has an eyeglass lens support adapted to receive the lens and an earstem attached to the eyeglass lens support. The kit also includes a goggle frame that has a lens support adapted to support the lens in a wearer's field of view, the lens support having a channel configured to receive the lens and secure the lens in place; and a padded layer attached to a posterior surface of the lens support, the padded layer configured to be pressed against a head of the wearer when in use. The lens is interchangeable between the eyeglass frame and the goggle frame such that the lens is configured to be alternatively supported by the eyeglass frame and the goggle frame.

In some embodiments of the third aspect, the eyeglass frame further comprises one or mote contact points configured to contact the unitary lens when the unitary lens is secured to the eyeglass frame. In some embodiments of the third aspect, between two or more contact points, a posterior surface of the eyeglass frame ex tends a protrusion distance rearward beyond a posterior extension of a posterior surface of the lens, the protrusion distance being less than or equal to about 4 mm. In a further embodiment, when the lens is secured to the eyeglass frame, the upper edge of the lens and a lower edge of the eyeglass lens support are spaced apart between two or more contact points to allow venting of the lens. In a further embodiment, a total length of the upper edge that is spaced apart from the frame is al least 20% of a total chord length of the upper edge of the lens.

In some embodiments of the third aspect, when the lens is secured to the eyeglass frame, a venting angle formed by an anterior surface of the frame and an upper edge of the lens is greater than or equal to 0 so that gaps between the upper edge of the lens and the lower edge of the frame between contact points are not visible when the eyewear is viewed straight on.

In some embodiments of the third aspect, an eyewear comprising the lens secured to the eyeglass frame or the lens secured to the goggle frame is configured to withstand a ballistic impact of a 0.25" ball having a speed of at least about 150 ft/s. In some embodiments of the third aspect, an eyewear comprising the lens secured to the eyeglass frame or the lens secured to the goggle frame is configured to withstand a ballistic impact of a .15 caliber cylindrical-shaped, chamfered-edge fragment having a speed of at least about 640 ft/s.

In some embodiments of the third aspect, between two or more contact points, a posterior surface of the eyeglass frame extends a protrusion distance rearward beyond a posterior extension of a posterior surface of the lens, the protrusion distance being less than or equal to about 3.2 times a center thickness of the lens. In a further embodiment, between two or more contact points, a posterior surface of the eyeglass frame extends a protrusion distance rearward beyond a posterior extension of a posterior surface of the lens, the protrusion distance being less than or equal to the center thickness of the lens. In some embodiments of the third aspect, the lens comprises a unitary lens.

BRIEF DESCRIPTION OF THE DRAWINGS

Throughout the drawings, reference numbers may be re used to indicate correspondence between referenced elements. The drawings are provided to illustrate example embodiments described herein and are not intended to limit the scope of the disclosure.

DETAILED DESCRIPTION

Figure 1A:
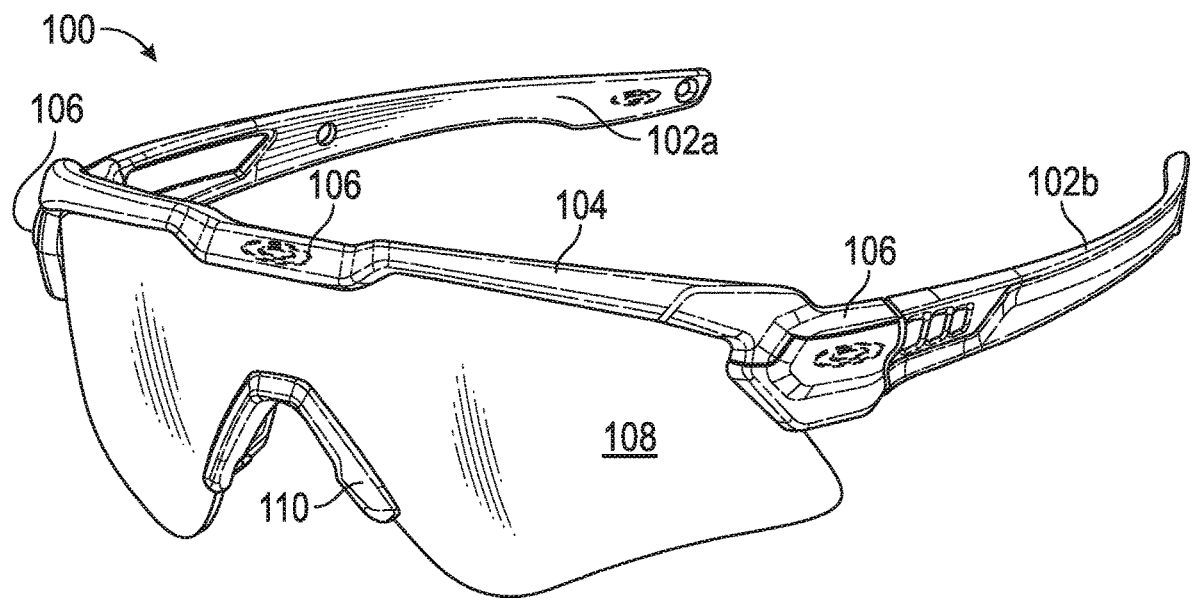
FIGS. 1A-1C illustrate front perspective views of example embodiments of eyewear.

While the present description sets forth specific details of various embodiments, it will be appreciated that the description is illustrative only and should not be construed in any way as limiting. Additionally, although particular embodiments may be disclosed or shown in the context of particular types of eyewear systems, such as unitary lens eyeglasses, dual lens eyeglasses having partial or full orbitals, and goggles, it is understood that any elements of the disclosure may be used in any type of eyewear system. Moreover, any elements of the disclosure may be used in any headworn support (i.e., a head worn article that can support one or more lenses in the wearer's field of view). For example, other types of headworn supports can include, but are not limited to, helmets, face masks, balaclavas, and breaching shields. Further, although embodiments disclosed herein can be used with eyewear that have removable and replaceable lenses, embodiments are also contemplated in which the eyewear are not intended to provide for removable or replaceable lenses. Although some embodiments are illustrated with lenses having "cylindrical" or "spherical" front and rear surfaces (surfaces which conform substantially to a portion of the surface of a sphere or cylinder, respectively), it will be understood by those having ordinary skill in the art that, in some embodiments, lenses having different surface geometries can be used. Additionally, it will be understood that lenses of many front elevational shapes and orientations in the as-worn position can be used, beyond those illustrated herein. In particular, either the front or rear surface of a lens may conform to the surface of a toroidal or other aspheric geometry. Any feature, structure, function, material, method, or step disclosed and/or illustrated in this specification can be used by itself or with or instead of any other feature, structure, function, material, method, or step disclosed and/or illustrated elsewhere in this specification. Each portion of this specification is contemplated to be interchangeable and no portion is indispensable or essential.

Generally, head worn supports with lenses, including eyewear such as eyeglasses and goggles, are configured to provide desired optical functionality for a wearer. These headworn supports (such as eye wear) may also be used to intercept light, wind, dust, etc. from directly in front of the wearer and peripherally along the sides. In use, however, the lens or lenses can become clouded through condensation on the inner surface of the lens (e.g., the surface nearest the face of the user), reducing the wearers visibility and/or degrading the optical performance of the lens. To reduce condensation on the lens, the head worn support can be configured to be vented using active or passive means. Venting can increase air flow at the inner surface or region of the lens and between the lens and the user, thereby reducing condensation. In passive venting systems, holes or other passageways may be introduced into the structures of the headworn support, such as frames, and/or lenses to provide a path for air to travel from one side of the headworn support (e.g., an exterior region) to the other (e.g., an interior region) to increase air flow. However, this may have the undesirable effect of allowing light to pass through such passageways into the eye of the user and/or allowing particles, dust, or debris through the holes to contact the user around the eye.

Some examples of headworn supports, such as eyewear, disclosed herein are configured to provide passive venting by providing one or more pathways between a lens and a frame and/or by providing a smooth rear profile to allow a laminar flow of air on a posterior surface of the lens. In certain implementations, the one or more passive-venting pathways provide a tortuous path between a frame and a lens of the headworn support to the eye of a wearer (e.g., they do not provide a direct path to the eye of the wearer from an exterior region). Thus, the headworn support provided herein can provide venting while reducing or preventing unwanted light, wind, particles, or other debris from contacting the eye of the user.

In some embodiments, a headworn support, such as an eyewear, is provided that includes a frame and a lens wherein a large proportion of the lens is unsupported by the frame such that a gap between the lens and the frame allows air to flow to provide passive venting. The gap is configured so that there is a tortuous path between the frame and the lens (e.g., there is no direct path between the frame and the lens to the eye of the user). In addition, when viewed from the front of the headworn support, the gap may not be visible to an observer. In addition, the headworn support can be configured to position the lens near the face of the user so that there is no direct path for light to travel to the eye of the user from the top of the headworn support. For example, light traveling downward passes through the lens to reach the eye of a user and does not reach the eye of the user without first passing through the lens. In some embodiments, the frame of the headworn support can be configured so that a portion of a posterior surface of the frame does not extend rearward from a posterior extension of the posterior lens surface. In certain embodiments, the frame of the head worn support can be configured so that a portion of the posterior surface of the frame extends rearward of from the posterior extension of the posterior lens surface, where the extension is less than or equal to about 4 mm, less than or equal to about 3.8 mm, less than or equal to about 3.5 mm, less than or equal to about 3.3 mm, less than or equal to about 3 mm, less than or equal to about 2.6 mm, less than or equal to about 2.25 mm, or less than or equal to about 2 mm. In certain embodiments, the extension can be less than or equal to about 3.2× a center thickness of the lens, less than or equal to about 3× the center thickness of the lens, less than or equal to about 2.5× the center thickness of the lens, less than or equal to about 2× the center thickness of the lens, less than or equal to about 1.5× the center thickness of the lens, less than or equal to about 1× the center thickness of the lens, or less than or equal to about 0.67× the center thickness of the lens. The portion of the frame that either does not extend past the posterior extension or that extends less than the stated distance past the posterior extension can have a total length that is at least 25% of the total chord length of the lens, al least 40% of the total chord length of the lens, at least 50% of the total chord length of the lens, at least 25% and/or less than or equal to about 80% of the total chord length of the lens, at least 35%, and/or less than or equal to about 70% of the total chord length of the lens, or al least 45% and/or less than or equal to about 60% of the total chord length of the lens. In some embodiments, this structure and/or other structures can produce laminar flow of air between the lens and the face of the user that can increase ventilation as compared to headworn supports having a frame that extends past the lens in the posterior direction towards the face of the user, thereby introducing turbulence into the flow of air. This feature may be particularly advantageous for headworn supports, such as eyewear and face masks, that generally conform to the shape of the face of the wearer because with such headworn supports there is typically less space between the face of the wearer and the lens. Where there is less space, airflow may be reduced, resulting in reduced venting of the lens and potentially increasing condensation on the lens compared to lenses that are generally positioned away from the face from a wearer.

In some embodiments, a headworn support, such as an eyewear, is provided that has an interchangeable lens configured to be used with eyeglasses and/or with goggles. For example, the frame of the eyeglasses can be semi-rimless and the lens can be secured to the frame using active and passive retention systems. The eyeglasses can include earstems to secure the eyeglasses in place on the head of the wearer so that the front frame does not contact the face of the wearer. This same lens can be removed from the frame of the eyeglasses and secured in a goggle frame. In some embodiments, the goggle can have full orbitals and can be configured to contact a face of the user, using, a bead strap to secure it in place.

Example Eyeglass

Figure 1B:
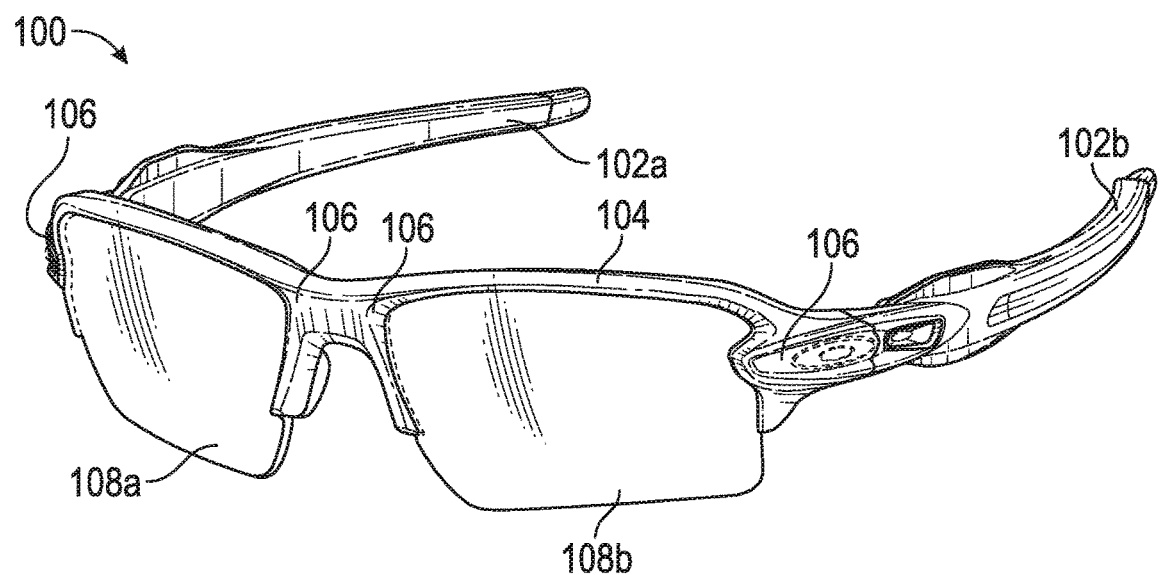
Figure 1C:
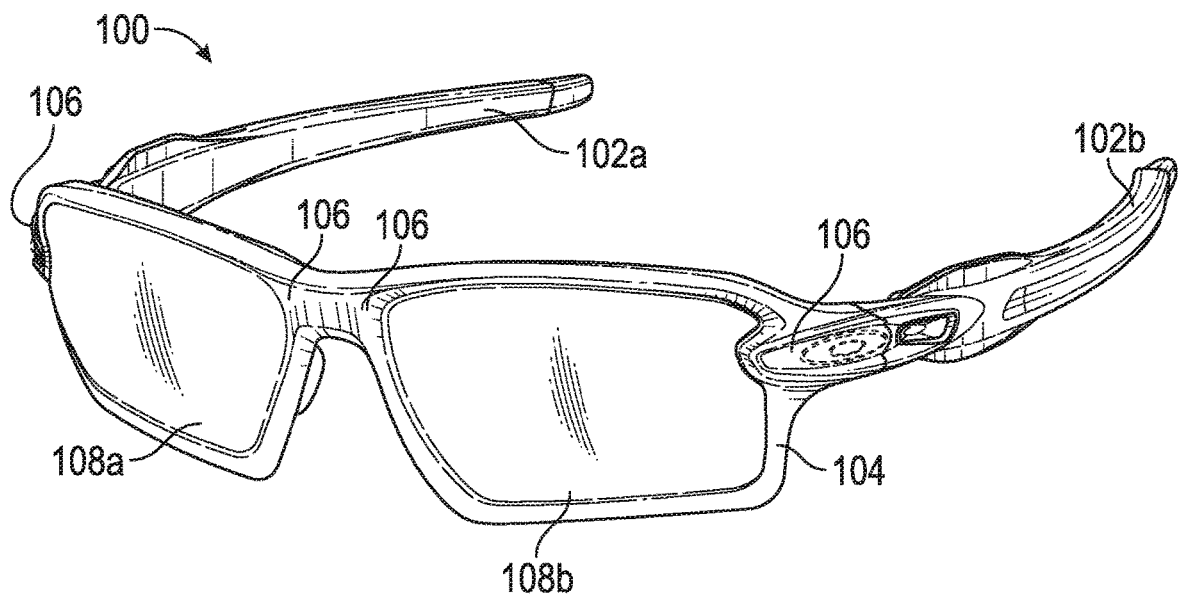

FIGS. 1A-1C illustrate front perspective views of example embodiments of eyewear, such as eyeglass 100. FIG. 1A illustrates an eyeglass 100 with a unitary lens 108 while FIGS. 1B and 1C illustrate eyeglass 100 with dual lenses 108a. 108b. FIGS. 1A and 1B illustrate eyeglass 100 with partial orbitals (e.g., a frame 104 of the eyeglass 100 does not extend entirely around the lens 108) while FIG. 1C illustrates eyeglass 100 with full orbitals (e.g., a frame 104 of the eyeglass extends entirely around the lenses 108a, 108b). The passive venting systems and interchangeable lens designs described herein can be applied to embodiments of eyeglasses with unitary lenses, dual lenses, partial orbitals, and full orbitals as well as other types of eyewear such as, but not limited to, goggles. Moreover, the passive venting systems and interchangeable lens designs described herein can be applied to other types of headworn supports such as, but not limited to, helmets, face masks, balaclavas, and breaching shields.

With reference to FIG. 1A, the eyeglass 100 comprises a pair of ear stems 102a, 102b, a frame 104, retention components 106, and a lens 108. The eyeglass 100 is configured such that the frame 104 and the lens 108 form a gap above the eyes of the user (e.g., around a plane that is generally parallel to the longitudinal or midsagittal plane and that intersects the eye of the user and the frame 104 and lens 108) as shown, for example, in FIGS. 3A-5B. As illustrated, these gaps are not visible when looking at the eyeglass 100 from the front. Thus, the eyeglass 100 provides an optically blind venting system, which can refer to a venting system that is not readily visible when viewing the eyeglass 100 straight on. The eyeglass 100 can be configured such that the lens 108 can be removed and replaced. However, in some embodiments, the lens 108 may not be removable or replaceable. The eyeglass 100 can include nose piece 110 attached to the lens 108 to nest on a nose of the wearer when in use.

The lens 108 or lenses 108a. 108b 102b can be plano lenses (e.g., not curved). The lens 108 or lenses 108a, 108b 102b can be linear (not curved) along a vertical plane (e.g., cylindrical or frusto-conical lens geometry). In some embodiments, the lens 108 or lenses 108a. 108b can be aligned substantially parallel with the vertical axis such that the line of sight is substantially normal to the anterior surface and the posterior surface of the lens. In some embodiments, the lens 108 or lenses 108a. 108b are angled downward such that a line normal to the lens is offset from the straight ahead normal line of sight by an angle φ. The angle φ of off set can be greater than about 0° and/or less than about 30°, or greater than about 10° and/or less than about 20°, or about 15°, although other angles φ outside of these ranges may also be used. Various cylindrically shaped lenses may be used. The anterior surface and/or the posterior surface of the lens 108 or lenses 108a. 108b can conform to the surface of a right circular cylinder such that the radius of curvature along the horizontal axis is substantially uniform. An elliptical cylinder can be used to provide lenses that have non-uniform curvature in the horizontal direction. For example, a lens may be more curved near its lateral edge than its medial edge. In some embodiments, an oblique (non-right) cylinder can be used, for example, to provide a lens that is angled in the vertical direction.

In some embodiments, the eyeglass 100 incorporates a canted lens 108 or canted lenses 108a. 108b mounted in a position rotated laterally relative to conventional centrally oriented dual lens mountings. A canted lens may be conceived as having an orientation, relative to the wearer's head, which would be achieved by starting with conventional dual lens eyeglass having centrally oriented lenses and bending the frame inwardly at the temples to wrap around the side of the head. When the eyeglass 100 is worn, a lateral edge of the lens wraps significantly around and comes in close proximity to the wearer's temple to provide significant lateral eye coverage.

A degree of wrap may be desirable for aesthetic styling reasons, for lateral protection of the eyes from flying debris, or for interception of peripheral light. Wrap may be attained by utilizing lenses of tight horizontal curvature (high base), such as cylindrical or spherical lenses, and/or by mounting each lens in a position which is canted laterally and rearwardly relative to centrally oriented dual lenses. Similarly, a high degree of rake or vertical tilting may be desirable for aesthetic reasons and for intercepting light, wind, dust or other debris from below the wearer's eyes. In general "rake" will be understood to describe the condition of a lens, in the as-worn orientation, for which the normal line of sight strikes a vertical tangent to the lens 108 at a non-perpendicular angle.

The lens 108 or lenses 108a. 108b can be provided with anterior and posterior surfaces and a thickness therebetween, which can be variable along the horizontal direction, vertical direction, or combination of directions. In some embodiments, the lens 108 or lenses 108a. 108b can have a varying thickness along the horizontal or vertical axis, or along some other direction. In some embodiments, the thickness of the lens 108 or lenses 108a, 108b tapers smoothly, though not necessarily linearly, from a maximum thickness proximate a medial edge to a relatively lesser thickness at a lateral edge. The lens 108 or lenses 108a. 108b can have a tapering thickness along the horizontal axis and can be decentered for optical correction. In some embodiments, the lens 108 or lenses 108a. 108b can have a thickness configured to provide an optical correction. For example, the thickness of the lens 108 or lenses 108a, 108b can taper from a thickest point at a central point of the lens 108 or lenses 108a, 108b approaching lateral segments of the lens 108 or lenses 108a, 108b. In some embodiments, the average thickness of the lens 108 or lenses 108a, 108b in the lateral segments can be less than the average thickness of the lens 108 or lenses 108a, 108b in the central zone. In some embodiments, the thickness of the lens 108 or lenses 108a, 108b in at least one point in the central zone can be greater than the thickness of the lens 108 or lenses 108a. 108b at any point within at least one of the lateral segments.

Various materials can be utilized in the manufacture of the frame 104, such as metals, composites, or relatively rigid, molded thermoplastic materials which are well known in the art, and which can be transparent or available in a variety of colors. In some embodiments, the frame 104 can be plastic and may comprise acetate, polycarbonate, or nylon. The frame can be configured to be relatively light, resilient, and resistant to ballistic impact.

The retention components 106 can be configured to removably secure the lens 108 to the frame 104, thereby allowing the wearer to interchange the lens 108 of the eyeglass 100. For example, the lens 108 can be interchanged for a different lens if the lens 108 becomes damaged or dirty, and the lens KB can be interchanged for a different lens having different optical properties depending on the conditions of use. The retention components 106 can be configured to retain the lens 108 on the frame 104 in the event of impact to the lens 108 (e.g., a ballistic impact).

The retention components 106 can comprise one or more stationary or passive retention mechanisms and/or one or more movable or active retention mechanisms for engaging the lens 108. In a stationary or passive retention mechanism, engagement can occur between interlocking structures of the frame 104 and the lens 108 upon the lens 104 being fitted against a portion of the frame 104. For example, a protrusion along an edge of the lens 108 can fit into a groove of the frame 104 without requiring other or movable components to limit one or more degrees of freedom of movement of the lens 108 relative to the frame 104. In a movable or active retention mechanism, engagement can occur after the lens 108 is fitted against the frame 104 by moving a locking structure from a disengaged position to an engaged position. In a movable or active retention mechanism, a separate component can be moved relative to the lens 108 and the frame KM to secure the lens KB relative to the frame 104.

The passive and/or active retention mechanism(s) 106 can be disposed along any portion of the boundary between the lens 104 and the frame 108. In the illustrated embodiment, the unitary lens 108 has a passive lateral connector, a passive medial connector, and an active lateral connector, as detailed further below. In some embodiments, as illustrated, between the passive and active retention mechanisms 106, the lens 108 and the frame KM can be configured to not contact one another. The space between the lens 108 and the frame 104 can provide for passive venting of the lens 108. Similarly, between the passive and active retention mechanisms 106, a posterior extension of the posterior surface of the frame can be configured so that it either does not extend rearward of an extension of the posterior surface of the tens 108 or it can be configured so that it extends rearward of this posterior extension less than or equal to about 4 mm, less than or equal to about 3.8 mm, less than or equal to about 3.5 mm, less than or equal to about 3.3 mm, less than or equal to about 3 mm, less than or equal to about 2.6 mm, less than or equal to about 2.25 mm, or less than or equal to about 2 mm. In certain embodiments, the extension can be less than or equal to about 3.2× a center thickness of the lens 108, less than or equal to about 3× the center thickness of the lens 108, less than or equal to about 2.5× the center thickness of the lens 108, less than or equal to about 2× the center thickness of the lens 108, less than or equal to about 1.5× the center thickness of the lens 108, less than or equal to about 1× the center thickness of the lens 108, or less than or equal to about 0.67× the center thickness of the lens 108. In some embodiments, the configuration of the posterior surface of the lens 108 and the posterior location and/or shape of the frame 104 can cooperate to facilitate a laminar flow of air across the posterior surface of the lens 108 to assist in venting the lens 108.

With reference to FIGS. 1B and 1C, the eyeglass 100 can include two lenses 108a and 108b, each lens 108a. 108b being configured to have a space between an upper edge of the lens 108a, 108b and the frame 104 to allow air to (low through the space. In addition, the frame 104 can be configured similar to the eyeglass 100 described with reference to FIG. 1A in that a posterior surface of the frame 104 can be configured to not extend rearward of the posterior extension of the posterior surface of the lens 108a, 108b or to extend less than the slated distances rearward of this posterior extension. With reference to FIG. 1C, the frame 104 and lens 108a. 108b can be configured such that there are gaps between the lens 108a, 108b and the frame 104 at any of a variety of locations around the frame 104, such as the orbitals. For example, gaps can exist above the eyes of the wearer, below the eyes of the wearer, and/or lateral of the eyes of the wearer as shown for example, in FIGS. 3A-5B. Additionally, for the eyeglass 100 with full orbitals, the posterior surface of the frame 104 can be configured to not extend rearward of the posterior extension of the posterior surface of the lens 108a. 108b or to extend less than the stated distances rearward of this posterior extension, where the posterior extension of the lens can be made in any direction (e.g., vertically upward, vertically downward, horizontally, or any combination of these).

In either dual or unitary lens embodiments of the eyeglass or goggle, the lens can comprise one or more surfaces, edges, or structures that can be engaged by the lens retention mechanisms 106 of the frame 104. The lens retention mechanism(s) 106 can comprise one or more active and/or passive engagement mechanisms such as those described herein. A stationary or passive lens retention mechanism can be formed between a complementary retention surf ace carried by the frame 104 and a retention surface of the lens 108, such as the edge of a slot, notch, projection or aperture hieing generally away from the frame 104 to provide an interference fit.

In certain embodiments, the lens 108 can be engaged and/or supported at least at both lateral sides and a central portion thereof. For example, a unitary lens 108 may be secured to and/or supported by the frame 104 using a first retention structure on the left side of midline and a second retention structure on the right side of midline. The retention structures 106 can include any of the clips or other mechanisms disclosed herein. A retention structure 106 may be located within the frame 104 (e.g., within the central one-third of the frame, such as on or near the vertical midline or medial plane of the eyeglass). A plurality of retention structures 106 (e.g., at least two, three, four, five, six, or seven or more) may be used, depending at least in part upon the targeted performance. In various implementations, the retention structures 106 can be symmetrically spaced apart along the length of the frame 104, or as a mirror image across the plane of symmetry (anatomical midline or medial plane).

The eyeglass 100 can be useful in various settings, including military settings in which the wearer may experience conditions that may cause condensation on the lens, where eyeglass 100 may be subject to dust or other debris, and/or where the eyeglass 100 may experience a ballistic impact. The ventilation provided by the eyeglass 100 can reduce or prevent fogging on the interior of the eyeglass 100. In some embodiments, an anti-fogging coating can be applied to the interior of the eyeglass 100 (e.g., to the lens 108) to reduce or prevent moisture fogging. Various types of anti-fogging coatings can be used (e.g., moisture absorption coatings, moisture sheer coatings, coatings based on urethanes, and/or coatings based on treated polysiloxanes).

FIGS. 2A-2D illustrate views of the example eyeglass 100 of FIG. 1A to demonstrate attachment of the lens 108 to the frame 104. The lens 108 comprises lateral and medial engagement sections 208a. 208b. 208c configured to mate with corresponding retention mechanisms 106a, 106b, 106c. In some embodiments, the lens 108 can include one or more first retention mechanisms (e.g., projections 208a, 208b, 208c) that can be coupled with (e.g., seated in) corresponding second retention mechanisms (e.g., terminal recesses 106a, 106b, 106c) of the frame 104. Further, the lens 108 can comprise an upper edge or boundary. In use, when the projections 208a-208c are fitted into the recesses 106a-106c of the frame 104, the upper edge or boundary of the lens 108 can be configured to be spaced apart from the frame 104, except around the projections 208a-208c. Thus, in some embodiments, such an arrangement can provide passive venting through the formed space while also providing a lens retention and stabilization. In some embodiments, the frame 104 includes features that contact the lens 108 for providing structural support, these contact points being in addition to the retention mechanisms 106a-106c. In such embodiments, the upper edge or boundary of the lens 108 can be configured to be spaced apart from the frame 104, except around the retention mechanisms 106a-106c and these contact points.

The retention mechanism 106c can be an active retention mechanism. The retention mechanism 106c can include a rotating door 202 and a protrusion 204, the protrusion being configured to pass through a locking receptacle 206 on the frame 104. The protrusion 204 can engage with the locking receptacle 206 on a lateral side of the frame 104. The protrusion 204 can comprise a protruding element attached to the door 202 which is rotatably movable between a first position in which the lens 508 may be freely positioned within or removed from the retention mechanism 106c, and a second position in which the lens 108 is locked within the retention mechanism 106c.

The retention mechanisms 106a, 106b can generally be passive mechanisms that receive projections 208a. 208b of the lens 108 such that the projections 208a, 208b are seated in the corresponding recesses formed by opposing walls of the retention mechanisms 106a. 106b. In use, the lens 108 can be slid into place by pressing the projections 208a. 208b into the corresponding recesses or openings of the retention mechanisms 106a, 106b. In this way, the lens 108 can be generally fitted into and retained within the retention mechanisms 106a, 106b in the frame 104 without also contacting other portions of the frame 104. Thus, in some embodiments, such an arrangement can provide passive venting through the gap formed between the portions of the lens 108 not in contact with the retention mechanisms 106a-106c and not in contact with the frame 104.

When fitted onto the frame 104, the first engagement portion 208a of the lens 108, comprising a laterally extending projection, can be seated within a groove or slot on the frame 104 formed by opposing walls of the retention mechanism 106a. Similarly, the second engagement portion 208b of the lens 108, comprising an angled projection, can be sealed within a groove on the frame 104 formed by opposing walls within the retention mechanism 106b. The first and second engagement portions 208a, 208b can have different configurations and may be recesses, for example. The retention mechanisms can have different configurations and may be projections, for example. These passive retention mechanisms and corresponding features of the lens 108 can have a variety of configurations, including recesses, surface contours, cutouts, projections, slots, apertures, and other such surface structures and may be formed in a variety of shapes and/or sizes. The retention mechanisms 106a, 106b are shown as a single aperture, but can be formed as a plurality of apertures.

The retention mechanisms 106a. 106b. 106c can be disposed at any point along the frame 104. Thus, although three retention mechanisms 106a. 106b. 106c are used in the embodiment of the eyeglass 100, other embodiments of the eyeglass 100 can be constructed that comprise two, four, or five or more retention mechanisms disposed along the frame 104. Moreover, while retention mechanisms 106a, 106b have been described as passive mechanisms, it is to be understood that one or both of retention mechanisms 106a, 106b can be active mechanisms. For example, one or both of retention mechanisms 106a, 106b can have structures and/or functionality similar to retention mechanism 106c.

In some embodiments, as illustrated, the door 202 of the active retention mechanism 106c is rotatable relative to the lens 108, the frame 104, and the earstem 102b; however, any other form of movement can be used instead of or in addition to rotation. In some embodiments, the retention mechanism 106c can be configured to pivot or slide relative to the frame 104 and/or earstem 102b. In some embodiments, the retention mechanism 106c can be pivotally coupled to a different portion of the frame 104. However, in the illustrated embodiment, the retention mechanism 106c is configured to rotate relative to the frame 104 and the earstem 102b to allow earstems 102a, 102b to be folded in without disengaging the retention mechanism 106c.

Figure 2A:
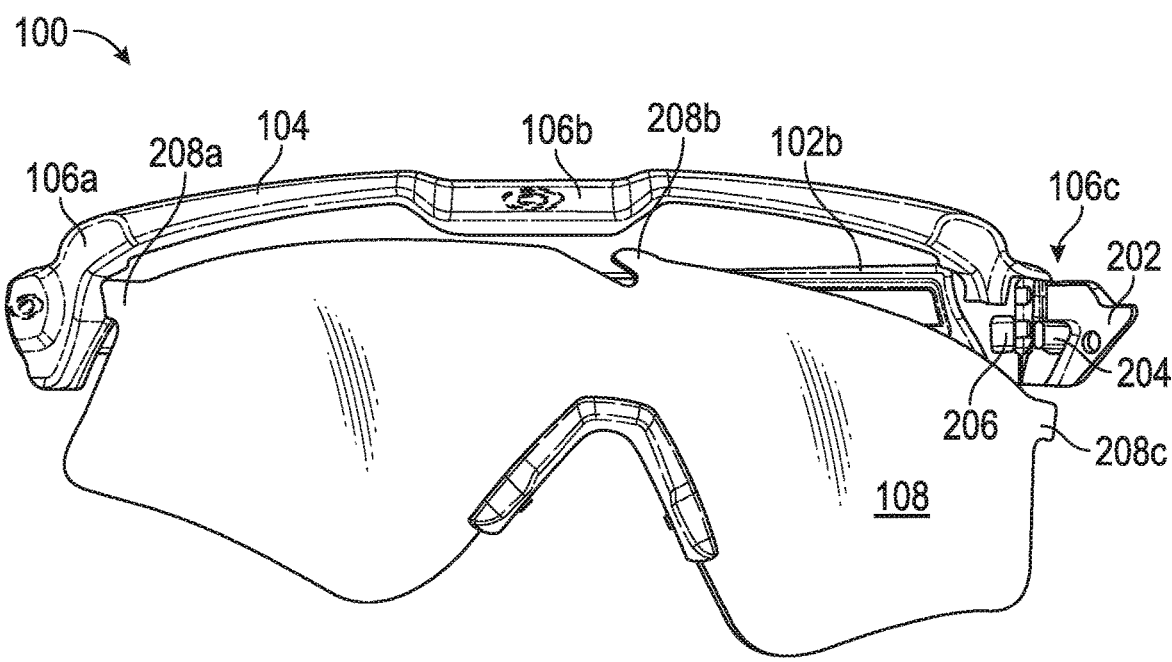
FIGS. 2A-2D illustrate views of the example eyewear of FIG. 1A to demonstrate attachment of a removable lens to a frame.
Figure 2B:
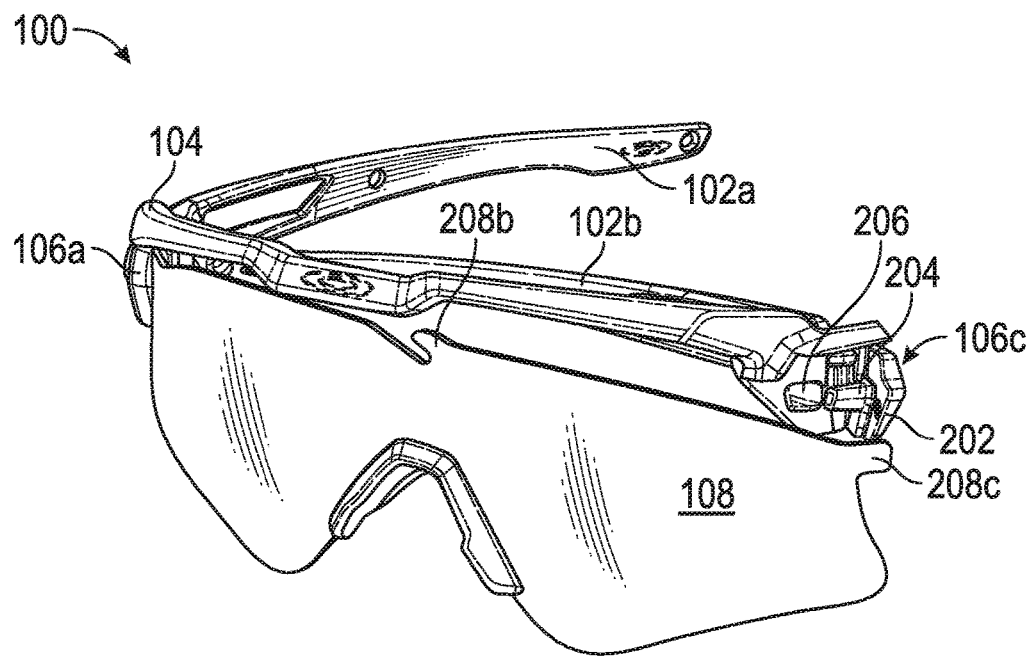
Figure 2C:
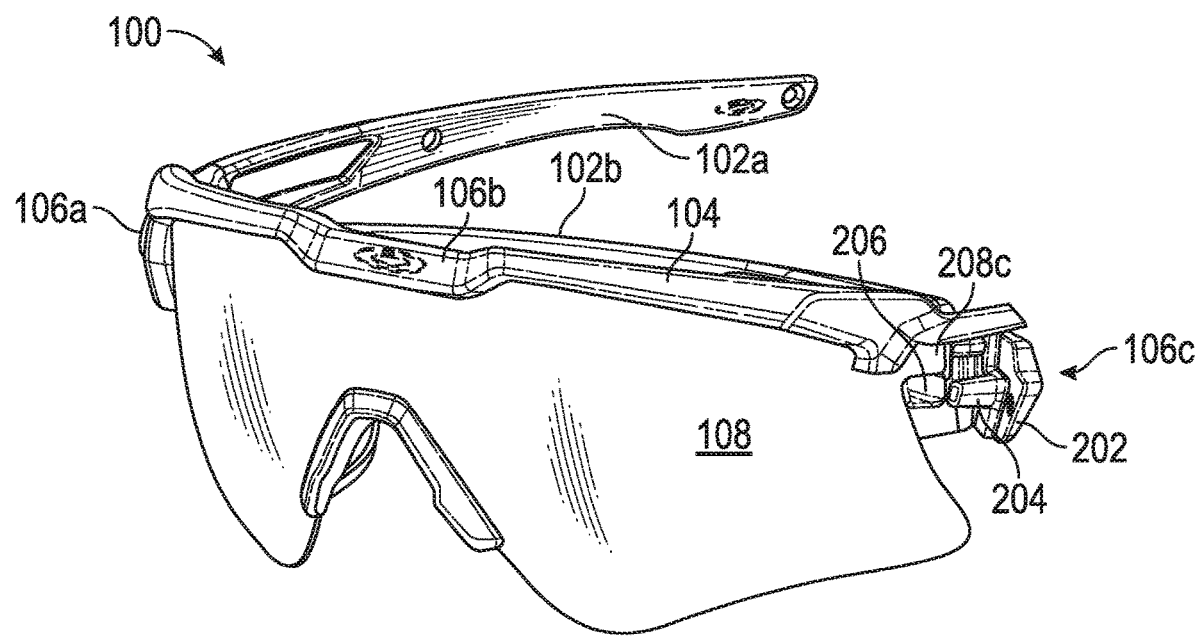
Figure 2D:
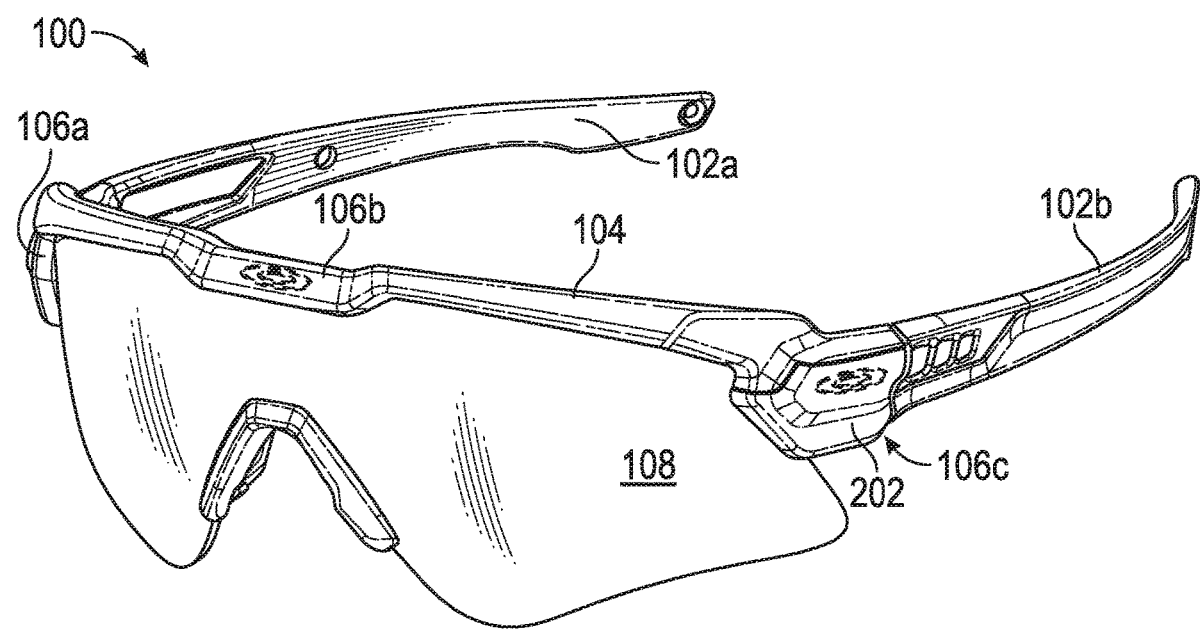

The passive retention mechanisms 106a. 106b can be configured such that the groove is at least partially defined by a pair of wall flanges of the frame 104. In some embodiments, the retention mechanism 106b can include a guide slot configured to align and to secure the lens at a midline of the eyeglass 100. For example, the transition from FIG. 2B to FIG. 2C illustrates the lens 108 being aligned and at least partially secured by engaging the protrusion 208b with the retention mechanism 106b. This has the added effect of properly aligning the protrusion 208c of the lens 108 so that it is ready for the active retention mechanism 106c to be locked into place by transitioning the door 202 from an open position to a closed position, as illustrated by the transition from FIG. 2C to FIG. 2D. In this closed position, the projection 204 restricts the movement of the lens 108 by restricting movement of the protrusion 208e. In this way, the lens 108 can be secured to the frame 104 using passive and active retention mechanisms.

Examples of Eyeglass Having Passive Venting

Figure 3A:
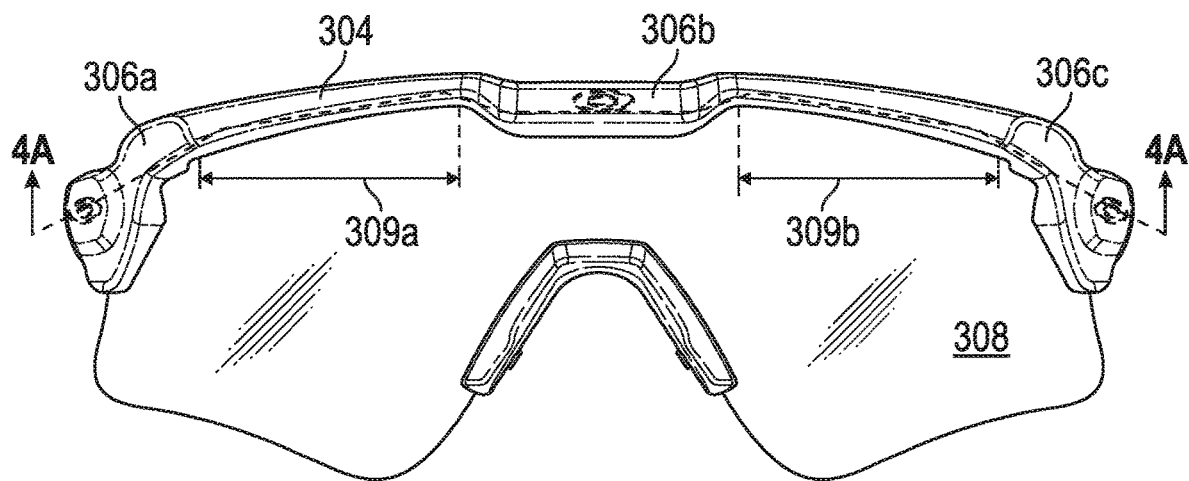
FIGS. 3A and 3B illustrate front elevational views of example embodiments of eyewear having a portion of a lens that is unsupported forming a gap between the lens and a frame of the eyewear.
Figure 3B:
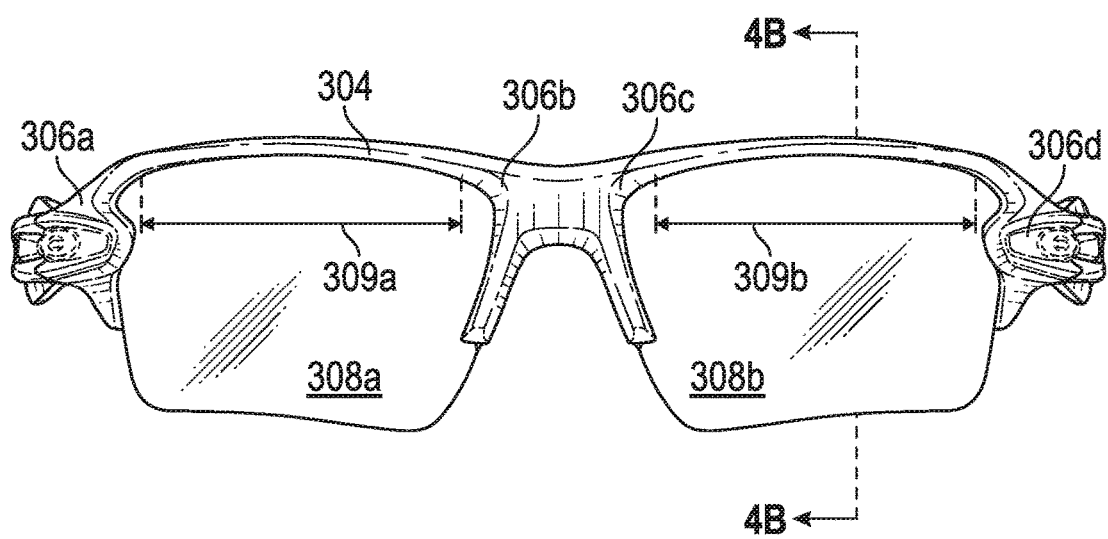

FIGS. 3A and 3B illustrate front elevational views of example eyewear, such as eyeglass 300 having a portion of a lens 308 that is unsupported forming gaps 309a, 309b between the lens 308 and a frame 304 of the eyeglass 300. The eyeglass 300 can incorporate the features and structures of eyeglass 100. As shown in the illustrated embodiment, the gap 309a can be formed on a first side of the frame 304 and the gap 309b can be formed on a second side of the frame 304. However, it is to be understood that the gap 309a and 309b can be combined into a single, continuous gap. The gaps 309a, 309b can be configured to allow air to flow around the lens 308. This exchange of air between the interior of the eyeglass 300 and the outside area reduces condensation on the posterior surface of the lens 308. The gaps 309a. 309b allow air to pass between the interior of the eyeglass 300 and the surrounding area. The gaps 309a, 309b can be located at or near the eyes of a user (e.g., above an area defined by a plane that is parallel to the longitudinal or mid-sagittal plane and that intersects an eye of the user). As shown in the illustrated embodiment, the gaps 309a, 309b are each continuous throughout its length. However, it is to be understood that the gaps 309a, 309b can be further divided into more sub-gaps such that gaps 309a and/or 309b are not continuous throughout their lengths. These sub-gaps can be formed, for example, where there are additional contact points between the contact points 306a, 306b, and/or 306c such that the frame 304 and the lens 308 can be configured to be spaced apart from one another at various locations. In some embodiments, one or both gaps 309a, 309b can be divided into two sub-gaps, three sub-gaps, four sub-gaps, five sub-gaps, six sub-gaps, or more. In some embodiments, one or both gaps 309a. 309b can be divided into at least two sub-gaps, at least three sub-gaps, al least four sub-gaps, al least five sub-gaps, at least six sub-gaps, or more. In some embodiments, the gaps 309a, 309b comprise about half of the total length of the upper edge of the lens 308. In some instances, the total length of the upper edge of the lens 308 can be the chord length of the upper edge of the lens 308 and the total length of the gaps 309a, 309b can be chord lengths of the gaps 309a, 309b. For example, an upper edge of the lens 308 may have a total chord length of about 170 mm and the total chord length of the gaps 309a, 309b can be about 85 mm with each gap 309a having a continuous chord length of about 425 mm. The total length or extent of the gaps (e.g., including sub-gaps) can be larger or smaller than this. For example, the total chord length of the gaps 309a, 309b relative to the total chord length of the lens 308 can be at least about 25%, at least about 40%, at least about 50%, at least about 25% and less than and/or equal to about 80%, at least about 35% and less than and/or equal to about 70%, or at least about 45% and less than and/or equal to about 60%. In some embodiments, the continuous or uninterrupted chord length (i.e., without any sub-gaps present such that the gap is undivided or unbroken) of al least one gap, such as gap 309a and/or gap 309b, relative to the total chord length of the lens 308 can be at least about 12.5%, at least about 20%, at least about 25%, at least about 12.5% and less than and/or equal to about 40%, at least about 57.5% and less than and/or equal to about 35%, or at least about 22.5% and less than and/or equal to about 30%. In some embodiments, the gaps 309 can be dispersed around the upper edge of the lens 308. In some embodiments, the gaps 309 at the upper edge of the lens 308 and the gaps between the lens 308 and the face of the user at the bottom of the eyeglass 300 can cooperate to produce a chimney effect that draws fresh air into an interior region of the eyeglass 300 from the bottom and expels air from the interior region of the eyeglass 300 from the top thereof. In some instances, the total length of the upper edge of the lens 308 can be the perimeter length (i.e., measured along the periphery), such as the are length, of the upper edge of the lens 308 and the total length of the gaps 309a, 309b can be the perimeter lengths, such as the arc lengths, of the gaps 309a. 309b. Accordingly, it is to be understood that any of the ratios and dimensioned above can be with respect to the perimeter lengths. In instances where the term "total length" is used, it should be understood that either the chord length or the perimeter length can be used.

In FIGS. 3A and 3B, the gaps 309a, 309b are generally hidden from view as the frame 304 serves to block a view of the gaps 309a, 309b. Thus, the gaps 309a. 309b are part of an optically blind venting system, or a venting system that includes gaps that are not visible when viewed straight on from a distance that is greater than or equal to about the width of the lens. In some embodiments, the gaps 309a. 309b are not visible when viewed straight on from about a foot or so away from the eyeglass 300 In some embodiments, only a portion of gaps 309a, 309b may be visible when viewed straight on from a distance that is greater than or equal to about the width of the lens, such that the gaps 309a, 309b are part of a primarily optically blind venting system. For example, the visible portion of the gaps 309a. 309b may be less than or equal to about 10%, of the total venting area defined between the upper edge 307 of the lens 308 and the lower edge of the frame 304. In this manner, 90% of the total venting area would not be visible when viewed straight on from a distance that is greater than or equal to about the width of the lens. In some embodiments, the visible portion of the gaps 309a. 309b may be less than or equal to about 20%, less than or equal to about 30%, less than equal to about 40%, of the total venting area defined between the upper edge 307 of the lens 308 and the lower edge of the frame 304

The eyeglass 300 can have multiple contact points where the frame 304 contacts the lens 308. These contact points can provide structural support and can be referred to as attachment points. The contact points 306a-306d can be attachment points because they provide structural support to the lens 308 or lenses 308a. 308b. The gaps 309a, 309b can be made up of a number of sub-gaps between contact points. The total gap length (e.g., the length of the gap 309a or 309b) can be the sum of the lengths of each sub-gap making up the gap 309a or 309b.

Figure 4A:
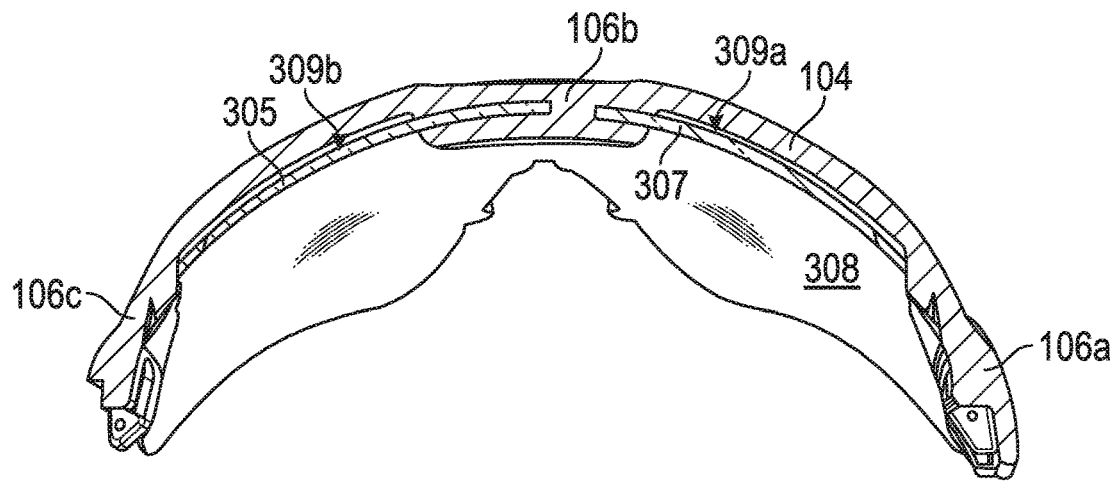
FIG. 4A illustrates a partial lop view of the example eyewear illustrated in FIG. 3A.

FIG. 4A illustrates a partial top view of the example eyeglass 300 illustrated in FIG. 3A. FIG. 4A illustrates the passive retention mechanism 106b interacting with the protrusion 305 of the lens 308. The upper edge 307 of the lens 308 is spaced apart from the frame 304 when the lens 308 is secured to the frame. The gaps 309a, 309b can be more clearly seen in this view.

Figure 4B:
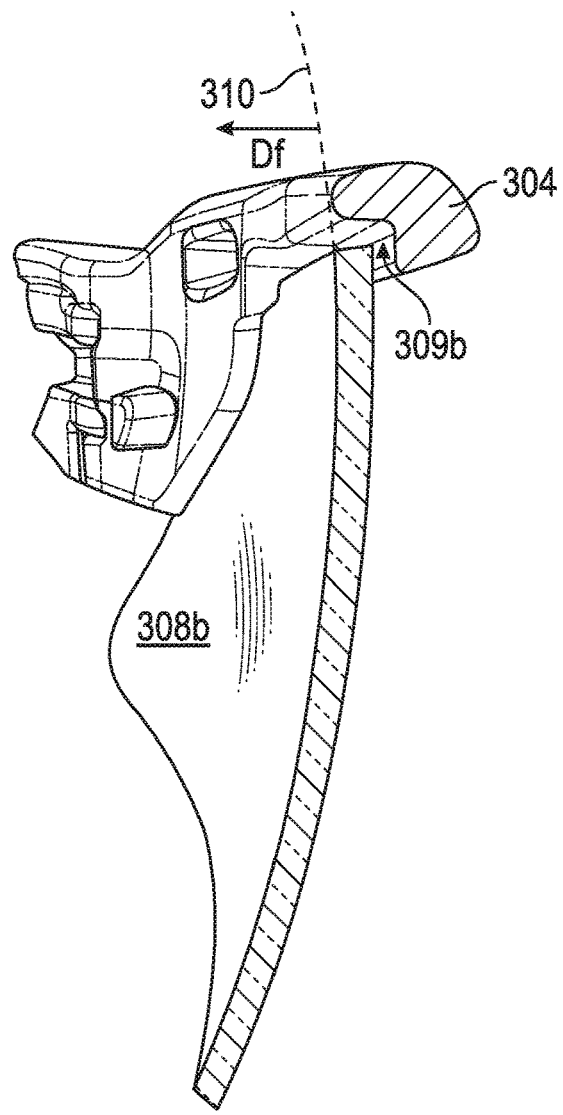
FIG. 4B illustrates a partial side view of the example eyewear illustrated in FIG. 3B.

FIG. 4B illustrates a partial side view of the example eyeglass 300 illustrated in FIG. 3B. The following disclosure, however, applies to both unitary lens embodiments and dual lens embodiments. Accordingly, the disclosure is provided with respect to a line of sight of a user rather than describing the eyeglass as a whole.

FIG. 4B illustrates the gap 309b between the frame 304 and the lens 308b when the lens 308b is secured to the eyeglass 300. A posterior extension 310 (e.g., a plane, a line, a curved surface, or a curved line) of the posterior surface of the lens 308b can be defined that acts as an imaginary extension of the posterior surface of the lens 308. This posterior extension 310 can define an imaginary plane, line, curve, or curved surface. A posterior surface of the frame 304 can be configured to extend rearward of the posterior extension 310 with a distance. Df, that is less than or equal to about 4 mm, less than or equal to about 3.8 mm, less than or equal to about 3.5 mm, less than or equal to about 3.3 mm, less than or equal to about 0.3 mm, less than or equal to about 2.6 mm, less than or equal to about 2.25 mm, or less than or equal to about 2 mm. Similarly, the distance, Df, can be defined in terms of the lens center thickness. For example, the lens 308 can have a center thickness that is at least about 1.25 mm and/or less than or equal to about 0.3.5 mm, at least about 1.5 mm and/or less than or equal to about 3 mm, or at least about 1.9 mm and/or less than or equal to about 2.7 mm. The rearward extension of the frame 304, Df, can be less than or equal to about 3.2× the center thickness of the lens 308, less than or equal to about 3× the center thickness of the lens 308, less than or equal to about 2.5× the center thickness of the lens 308, less than or equal to about 2× the center thickness of the lens 308, less than or equal to about 1.5× the center thickness of the lens 308, less than or equal to about 1× the center thickness of the lens 308, or less than or equal to about 0.67× the center thickness of the lens 308. In some embodiments, the posterior surface of the frame 304 is configured to not extend rearward of the posterior extension 310 (e.g., the posterior extension 310 does not intersect the frame 304 or Df≤0). The posterior extension 310 generally extends the shape of the posterior surface of the lens 308 wherein the lens 308 can be piano or can conform to a curved shape such as, for example and without limitation, a spherical shape, a right circular cylinder, a frusto-conical shape, a toroid, an elliptic cylinder, an ellipsoid, an ellipsoid of revolution, other asphere or any of a number of other three dimensional shapes described elsewhere herein. By limiting the extension of the frame 304 past the posterior extension 310, the eyeglass 300 can reduce condensation by allowing air flow to form a laminar flow. This can be contrasted with a frame that extends significantly rearward of a posterior extension of a lens which could cause turbulent air flow, reducing the flow of air and thereby reducing the anti-fogging characteristics of the eyeglass.

Figure 5A:
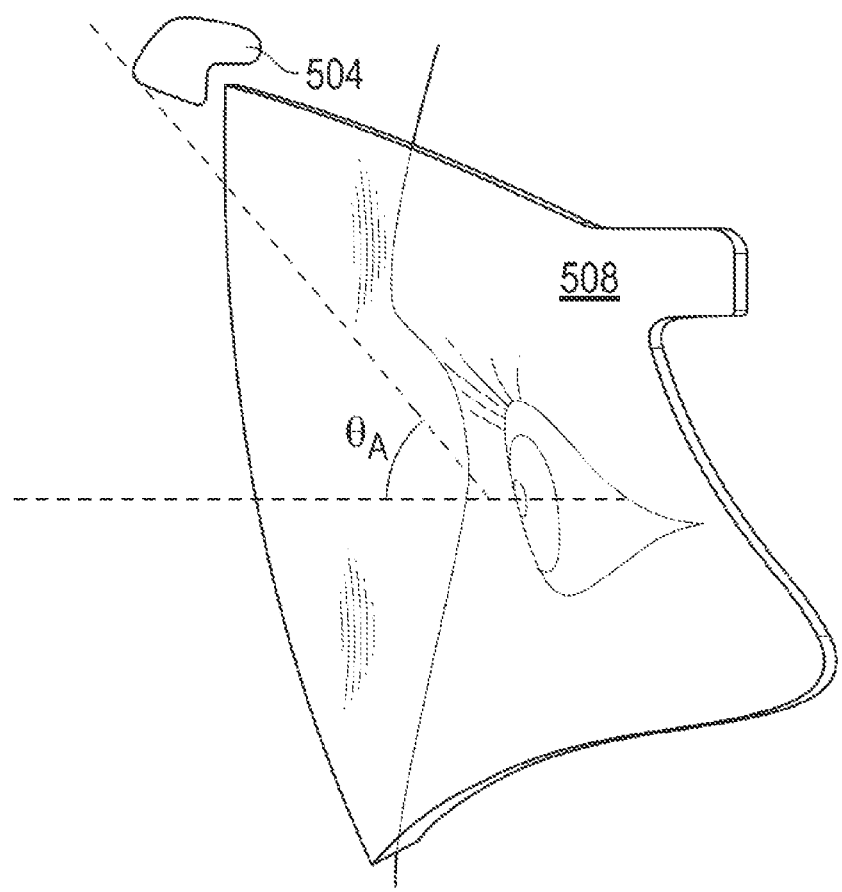
FIGS. 5A and 5B illustrate partial views of a lens and a frame with respect to an eye of a user to illustrate venting angles and illumination angles.
Figure 5B:
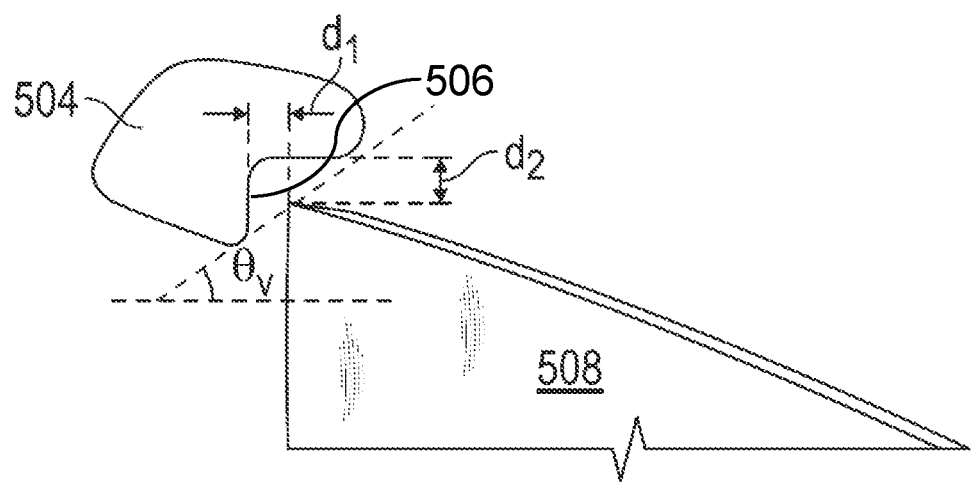

FIGS. 5A and 5B illustrate partial views of a lens 508 and a frame 504 with respect to an eye of a user to illustrate venting angles and illumination angles. For example, FIG. 5A illustrates a cross-section of the frame 504 above an eye of a user. The location and configuration of the frame 504 at that location can be configured so that there is a tortuous path to the user's eye (e.g., there is no direct path for light to travel to the user's eye without first passing through the lens 508). This may be advantageous to reduce or prevent undesirable stray light from entering the user's vision. The angle from the user's eye to the edge of the frame 504 can be referred to as the illumination angle, $\theta_A$. In some embodiments, the illumination angle can be less than or equal to about 48 degrees. In some embodiments, the illumination angle can be at least about 40 degrees and/or less than or equal to about 55 degrees, al least about 44 degrees and/or less than or equal to about 52 degrees, or at least about 46 degrees and/or less than or equal to about 50 degrees. The frame 504 and lens 508 can be configured to be relatively close to the face of the wearer so that light cannot travel in a straight line to the user's eye from above the user's eye without first travelling through the lens 508. As noted above, features of the frame 504, such as its relative relationship to the lens 508 (e.g., the presence of gaps forming a passive venting system which can be optically blind), can be used in any type of eyewear including, but not limited to, a unitary lens eyeglass, a dual lens eyeglass, an eyeglass with partial orbital, an eyeglass with full orbitals, and a goggle. In addition or in the alternative, features of the frame 504, such as its relative relationship to the lens 508, can be used with any other type of head worn support including, but not limited to, helmets, face masks, balaclavas, and breaching shields. In embodiments where the frame 504 extends around the entire periphery of the lens 508, the illumination angle can also refer to angles that are below the horizon as well as angles that extend temporally relative to a plane parallel to the longitudinal or mid-sagittal plane. The frame 504 can be configured to provide illumination angles that in turn allow a desirable amount of peripheral vision to the wearer. For example, the frame 504 and lens 508 can be configured to provide each eye a field of view that at least covers a circle having a radius greater than or equal to about 20 mm centered on a horizontal centerline and that is about 32 mm from the vertical centerline as measured at the lens 508.

FIG. 5B illustrates a close-up view of the cross-section of the frame 504 above an eye of the user. The gap between the lens 508 and the frame 504 is configured to be at least about 1 mm wide (e.g., d1 and d2 are about 1 mm). In some embodiments, the gaps d1 and d2 can be at least about 0.5 mm and/or less than or equal to about 3 mm, at least about 0.7 mm and/or less than or equal to about 2, mm at least about 0.8 mm and/or less than or equal to about 12 mm. The gap d1 can be formed between a posterior surface 506 of frame 504 (the posterior surface 506 facing toward a wearer's head in an as-worn position) and an interior surface of lens 508 facing away from the wear's head in an as-worn position. The venting angle, $\theta_V$, can be defined as the angle from the horizon for a direct path through the gap formed by the frame 504 and the lens 508. In some embodiments, the venting angle is al least about 32 degrees, in various implementations, the venting angle can be greater than 0 (e.g., where positive angles are angles measured vertically upward from horizontal). The venting angle can be at least about 5 degrees and/or less than or equal to about 60 degrees, at least about 10 degrees and/or less than or equal to about 50 degrees, or at least about 20 degrees and/or less than or equal to about 40 degrees. Because this angle is positive, debris, particles, and dust will be directed away from the eyes of the user. Similarly, because this angle is positive, there is no direct path through the gap to the eye of the user.

The venting angle and illumination angle formed by the lens 508 and the frame 504 cooperate to increase passive venting and reduce stray light and particulates at the user's eye. The gap can increase air flow across the posterior surface of the lens 508 while the frame 504 mid lens 508 act to protect the user's eyes from light and debris.

Example Removable Lens Retention

Figure 6:
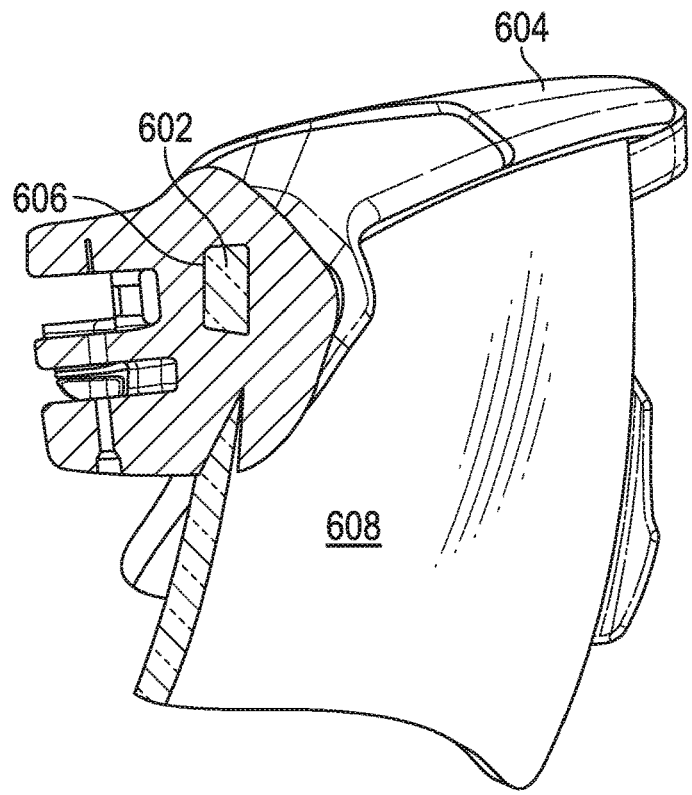
FIG. 6 illustrates a partial view of a lateral passive retention mechanism of a frame for a lens.
Figure 7:
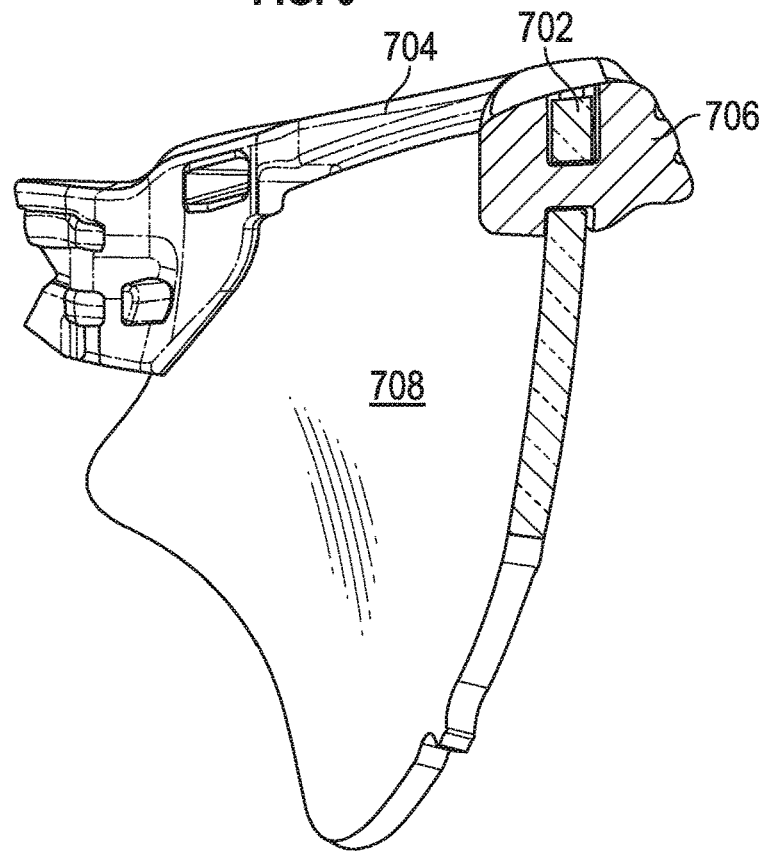
FIG. 7 illustrates a partial view of a passive retention mechanism near a midline of a frame for a lens.
Figure 8:
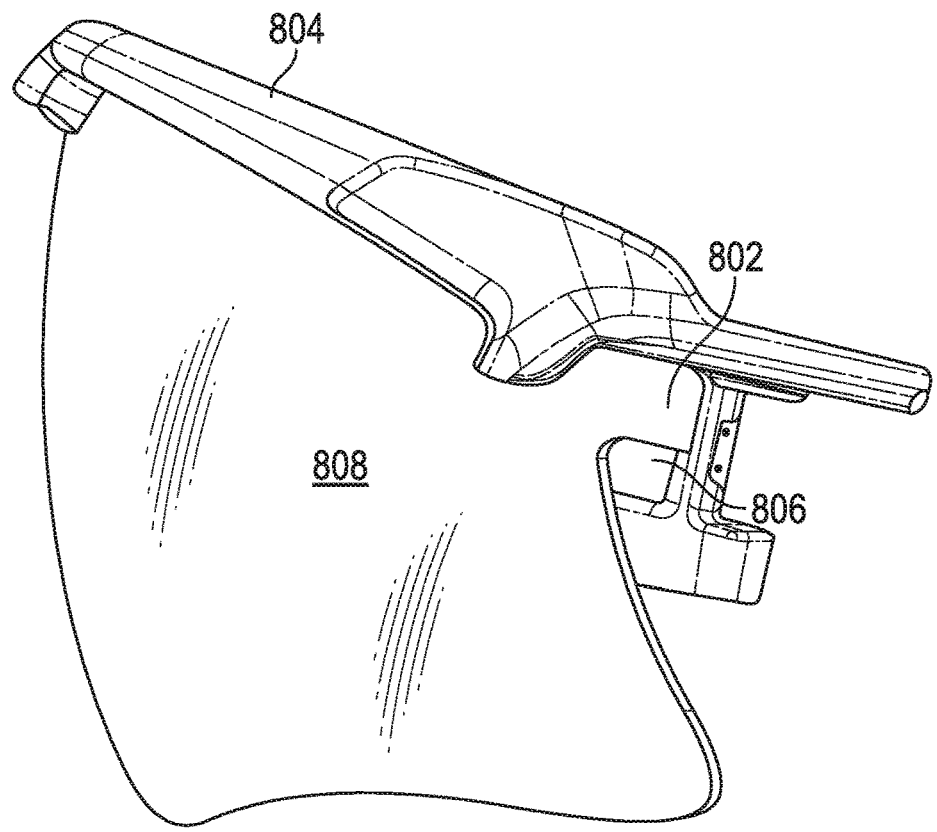
FIG. 8 illustrates a view of a lens situated in a frame having an active retention mechanism on a lateral portion of the frame.
Figure 9A:
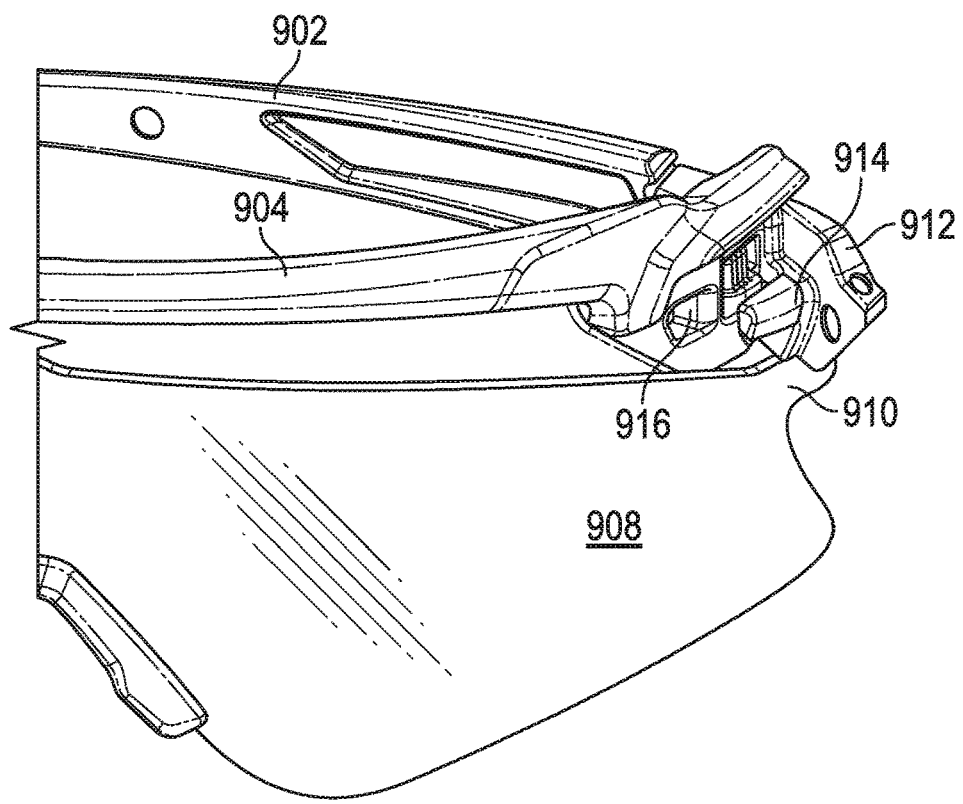
FIGS. 9A-9D illustrate several views of an active retention mechanism of a frame securing a lens to the frame.
Figure 9B:
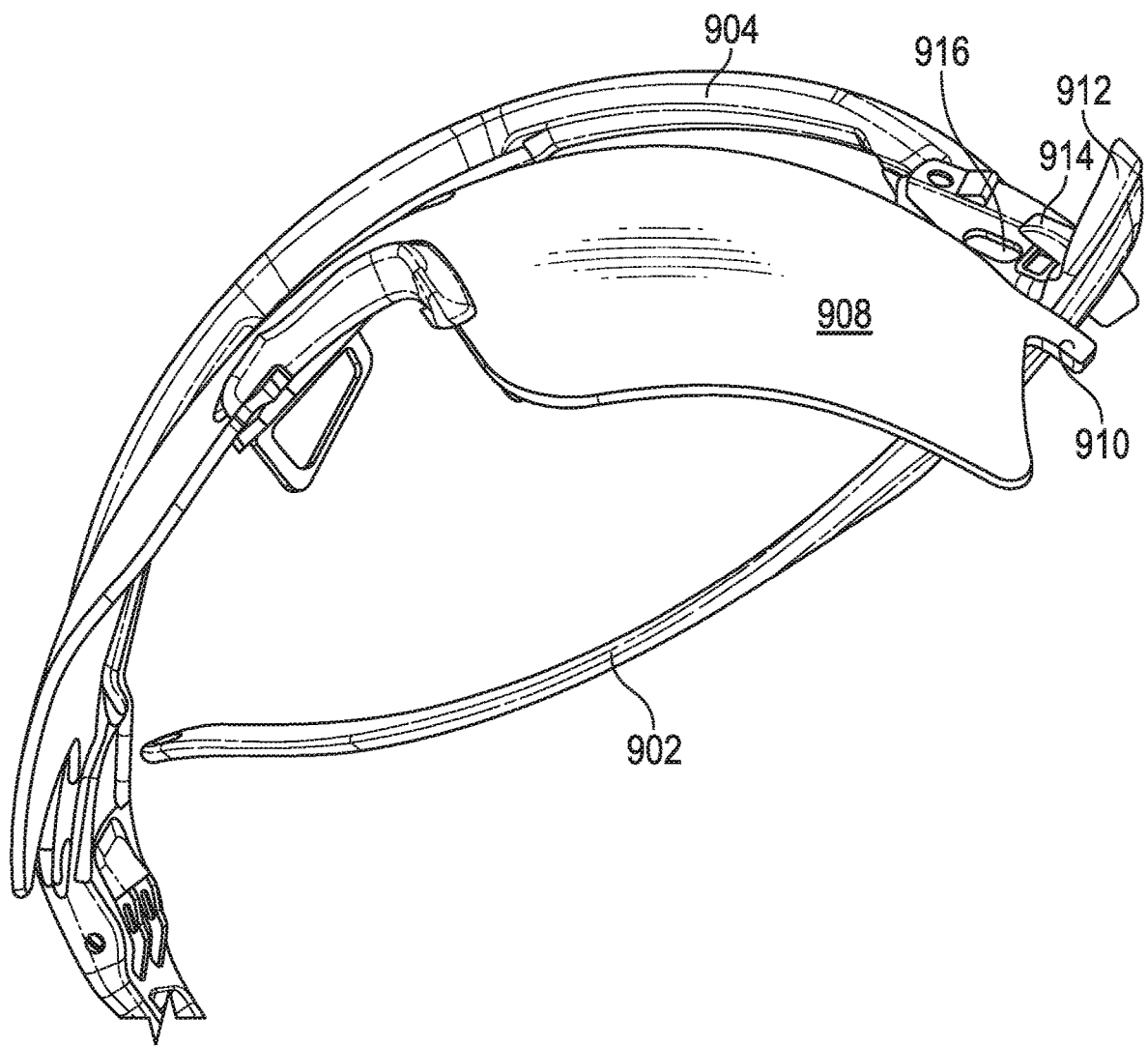
Figure 9C:
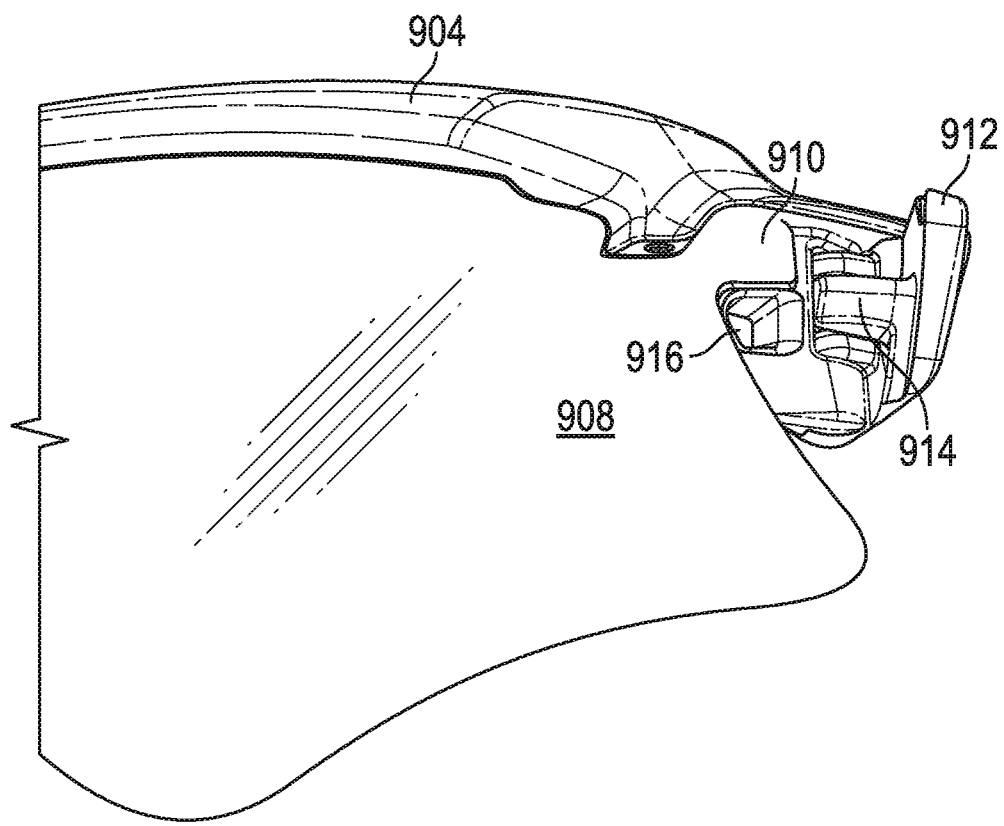
Figure 9D:
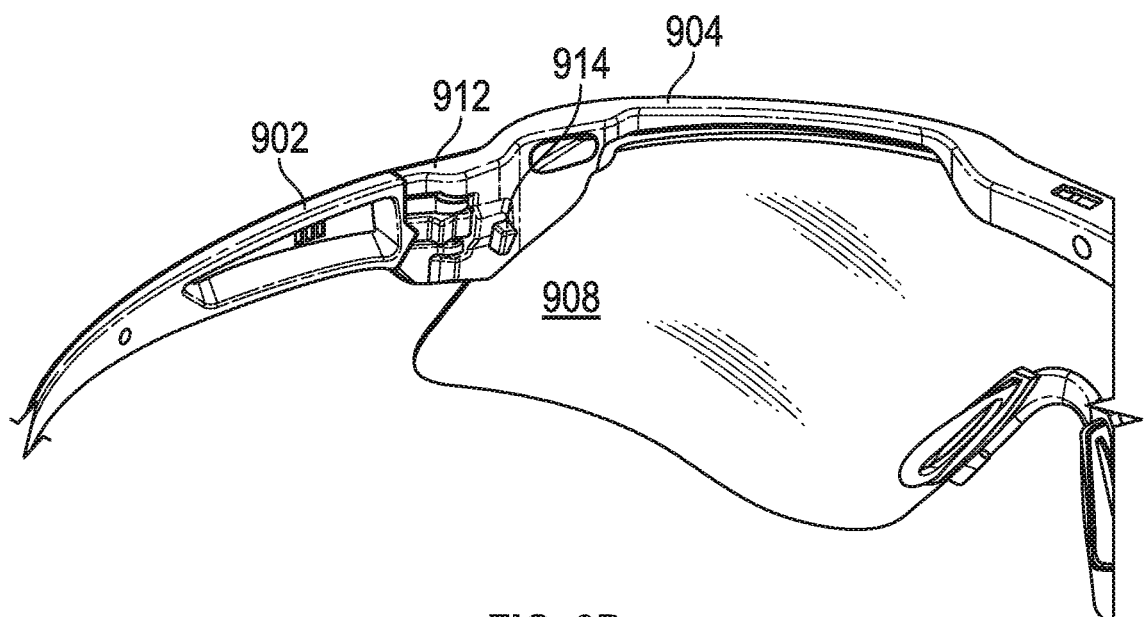

FIG. 6 illustrates a partial view of a lateral passive retention mechanism 606 of a frame 604 for a lens 608. As described herein, the lens 608 can include a protrusion 602 that is configured to seat within a receptacle 606 formed in the frame 604 of eyewear, such as the illustrated eyeglass. This lateral retention mechanism can act to align and to secure the lens 608 in the eyewear, allowing for a single active retention mechanism, described herein with reference to FIGS. 9A to 9D. FIG. 7 illustrates a partial view of a passive retention mechanism 706 near a midline of a frame 704 for a lens 708. As described herein, the lens 708 can include an angled protrusion 702 that is configured to sit within a groove 706 formed within the frame 704. This midline retention mechanism provides additional support and aligns the lens 708 when the lens is in use and when the lens is installed. FIG. 8 illustrates a view of a lens 808 situated in a frame 804 having an active retention mechanism 806 on a lateral portion of the frame 804. As described herein, the passive retention mechanisms act to align the lens 808 so that the protrusion 802 is properly situated to allow the active retention mechanism, described heroin with reference to FIGS. 9A to 9D, to lock the lens 808 in place relative to the frame 804.

The frame can include one or more contact points where the frame makes contact with the lens. One or more of these contact points can be attachment points, or points where the frame provides structural support to the lens (e.g., through an interference fit). An attachment point can be an active attachment point (e.g., an active retention mechanism) or a passive attachment point (e.g., a passive retention mechanism). The frame can include one or more passive attachment points and/or one or more active attachment points. In certain implementations, the attachment points can be the only locations where the lens contacts the frame of an eyewear. In various implementations, portions of the frame between the contact points do not contact the frame and form a gap between the frame and the lens to provide passive venting for the eyewear, as described elsewhere herein.

Example Active Retention Mechanism

FIGS. 9A-9D illustrate several views of an active retention mechanism of a frame 904 securing a lens 908 to the frame 904. The active retention mechanism includes a door 912, a projection 914, and a hinge that allows the door to pivot or otherwise move, wherein the door is configured to have a contour that matches the frame 904 and the earstem 902, to provide an aesthetically pleasing configuration when locked. The lens 908 includes the protrusion 910 that slides or otherwise moves into place when the lens is properly sealed in the passive retention mechanisms described herein, and as illustrated in the transition from FIG. 9B to FIG. 9C. Once the lens 908 is in place, the door 912 can transition to a closed state from an open state so that the projection 914 engages with the receptacle 916. This is shown in the transition from FIG. 9C to FIG. 9D, which shows a near view of the active retention mechanism locked in place.

When the active retention mechanism is locked in place, the earstem 902 can rotate freely from a folded state (e.g., approximately parallel to the frame 904) to an extended state (e.g., approximately perpendicular to the frame 904). This configuration provides a dual hinge action, wherein the door 912 has a first hinge around which it pivots and the earstem has a second hinge around which it pivots. Thus, when the door 912 is closed or locked into position, the earstem 902 can rotate without disengaging the active retention mechanism. However, when the earstem 902 is in the extended position, the door is prevented from opening. In this way, the active retention mechanism can be made to be locked so as to prevent the lens 908 from being accidentally removed from the frame 904. Similarly, when the door 912 is open and the earstem 902 is folded in, pivoting the earstem 902 to an extended position will act to close the door 912. Thus, the earstem 902 can be used to assist in locking the active retention mechanism in place to secure the lens 908.

Many other embodiments of the active retention mechanism are possible as well. For example, various systems have been designed that enable a wearer to quickly modify eyewear using replaceable components, earstems, and/or lenses, such by using the systems disclosed in U.S. Pat. Nos. 4,730,915, 5,387,949, and 7,347,545, and U.S. Publication No. 2013/0077042, the entirely of the disclosure of each of which is incorporated herein by reference. In some embodiments disclosed heroin, support can be provided to a replaceable or removable lens at three or more points on the lens to enhance the ballistic resistance and lens stability of an eyeglass or goggle. Some examples of support features are shown in U.S. Pat. No. 7,954,942, issued on Jun. 7, 2011, the entirely of which is incorporated herein by reference. Farther examples of support features are shown in U.S. Pat. No. 8,192,015, issued on Jun. 5, 2012, U.S. Pat. No. 8,469,510, issued on Jun. 25, 2013, and U.S. Pat. No. 8,881,316, issued on Nov. 11, 2014, the entireties of each of which are incorporated herein by reference.

Some embodiments described herein can advantageously securely retain the lens relative to the frame while generally providing passive venting capabilities along with desirable optical characteristics. For example, the lens can be secured to and/or supported by the frame in a manner that generally preserves the as-molded geometry of the lens while preventing stray light from entering the user's eye. This can be accomplished while providing gaps between the frame and the lens to provide venting. Some embodiments disclosed herein can advantageously provide an eyeglass or goggle in which the lens and/or ear stems can be easily removed and replaced by the wearer while enabling the wearer to mount the lens and providing superior ballistic resistance and lens stability.

Example Goggle

FIGS. 10A-10D illustrate several views of an example goggle 1000 configured to be used with embodiments of the lenses described herein. The goggle 1000 is configured to receive the lens 1008 within a support structure, such as a goggle frame 1004. The lens 1008 comprises an arcuate unitary lens which extends across both of the wearer's right and left eye fields of view. The lens 1008 is supported by the frame 1004 wherein the frame 1004 is configured to surround the lens 1008 and configured to contact the head of a user. The lens 1008 and the frame 1004 are both configured with a downwardly concave indent or nosepiece opening for receiving the nose. The rear surface of the frame 1004 is covered with a foam component 1005 or other compressible material, and is adapted to contact the wearer's face. Further, the elastic strap 1001 is connected to the opposing sides or ends of the frame 1004 so that the wearer can fit and wear the goggle on their bead.

When worn, the surface of the foam component 1005 or other compressible material disposed at the rear of the goggle 1000 makes contact with the wearer's face. This wearer-contacting surface has a radius of curvature in the horizontal plane that is adapted to conform from side to side of the wearer's face.

In use, the wearer can position the goggle frame 1004 onto her face and adjust the elastic strap 1001 around the back of her head in order to firmly, but comfortably secure the goggle frame 1004 in place. The foam component 1005 is intended to contact the wearer's face and allow the goggle 1000 to conform to the surface of the wearer's face. The goggle frame 1004 can be rigid or semi-rigid. The goggle frame 1004 can be pliable and flexible to allow the lens 1008 to be easily inserted and removed. The goggle frame 1004 can include a groove or channel 1012 around an interior portion of the goggle frame 1004 to provide a guide for the lens 1008. The lens 1008 can be positioned within the groove or channel 1012 structure, wherein the groove or channel 1012 structure includes one or more features that act as passive retention mechanisms to secure the lens in place during use. The goggle frame 1004 can be worn on the head of the user without the lens 1008, if so desired.

Figure 10A:
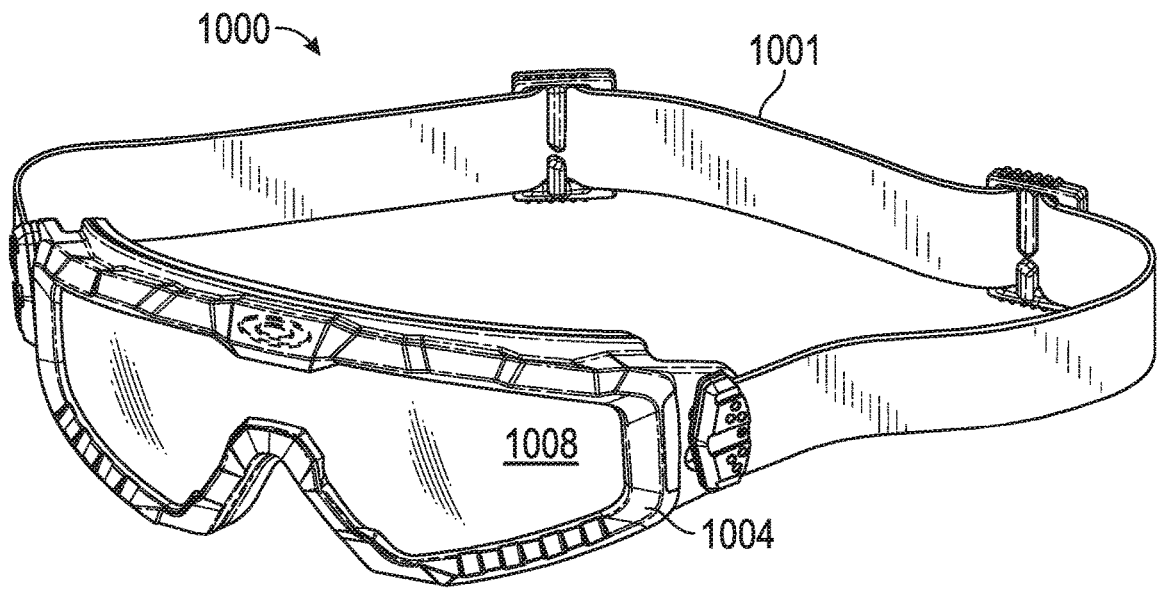
FIGS. 10A-10D illustrate several views of an example goggle configured to be used with embodiments of the lenses described herein.
Figure 10B:
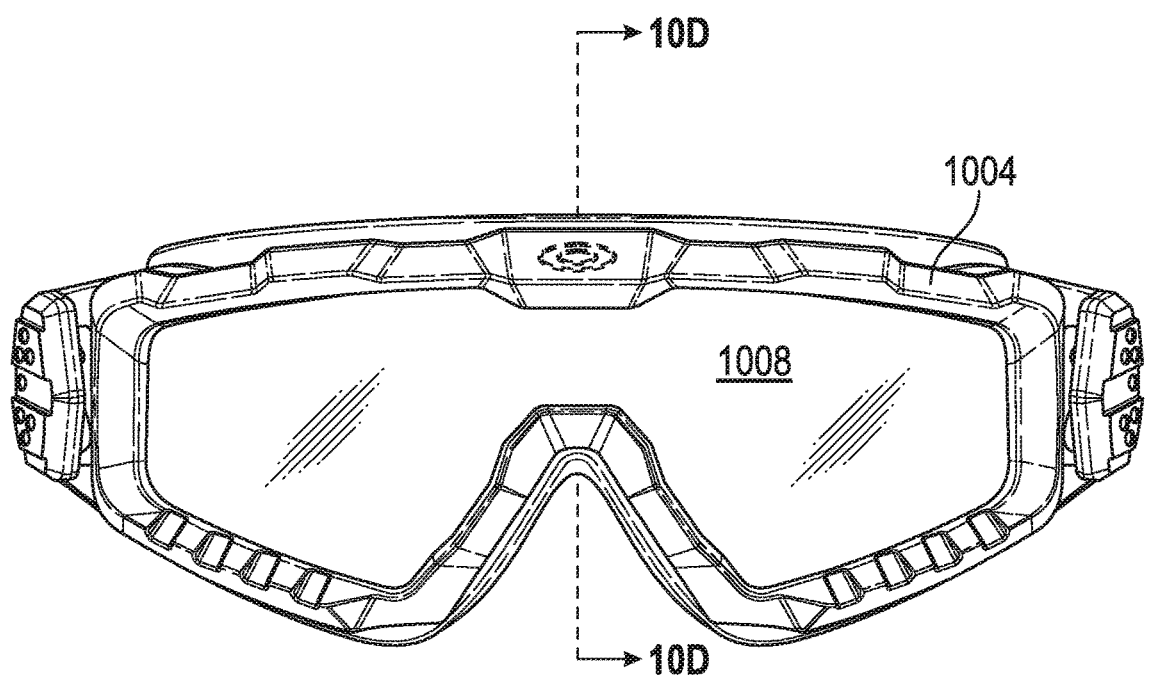
Figure 10C:
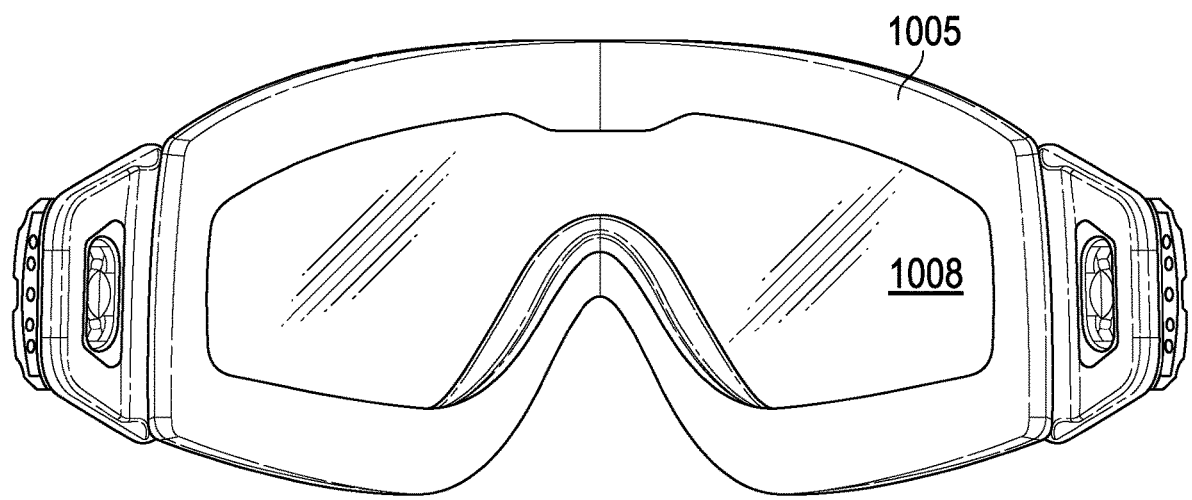
Figure 10D:
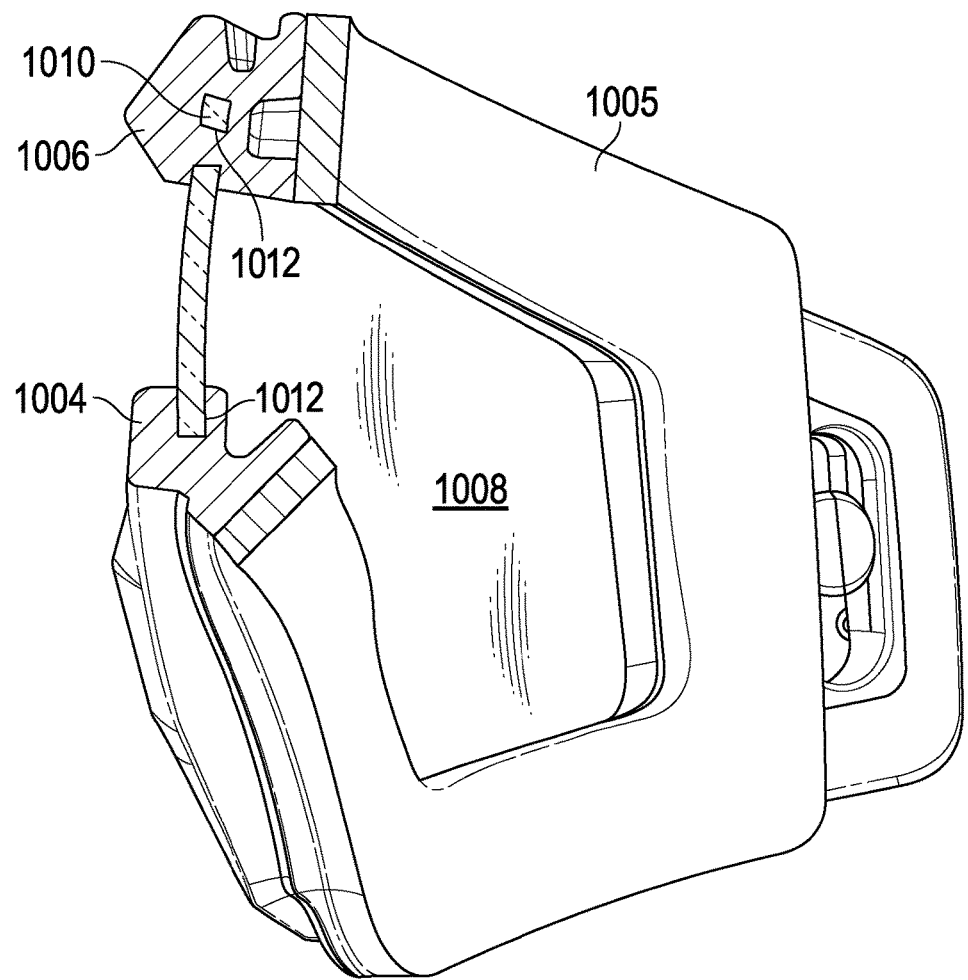

FIG. 10D illustrates a cress-sectional side view of the goggle 1000. As shown, the lens 1008 of the goggle 1000 is mounted in the goggle frame 1004 with the features that allow it to be secured in an eyeglass frame acting to secure it in the goggle frame. For example, the lens 1008 can include protrusion 1010 configured to sit within a passive retention mechanism 1006 of the goggle frame 1004.

In some embodiments, the interchangeable lens structure 1008 can provide at least one interconnection point or engagement section 1010 between the lens 1008 and the retention mechanism 1006 where the lens 1008 is secured to the goggle frame 1004. The interchangeable lens structure 1010 can comprise one or more stationary structures, which can be used in combination to retain the lens 1008 in a mounted position within the goggle 1004. Other examples of an interchangeable lens structure 1008 with a goggle frame 1004 are provided in U.S. Pat. No. 8,800,067, issued Aug. 12, 2014, entitled "Eyewear with Interchangeable Lens Mechanism." the entirety of which is incorporated herein by reference.

In some embodiments, the goggle frame 1004 can incorporate a passive venting system. For example, the goggle frame 1004 can include structures, such us gaps, similar to those described above in connection with frames 104, 304. In some embodiments, the gaps can be generally hidden from view as the frame 1004 serves to block a view of the gaps. Thus, the gaps can be part of an optically blind venting system, or a venting system that includes gaps that are not visible when viewed straight on from a reasonable distance (e.g., about a foot or so away from the goggle 1000). In some embodiments, only a portion of gaps may be visible when viewed straight on from a reasonable distance such that the gaps 309a. 309b are part of a primarily optically blind venting system.

Example Headworn Support

Figure 13:
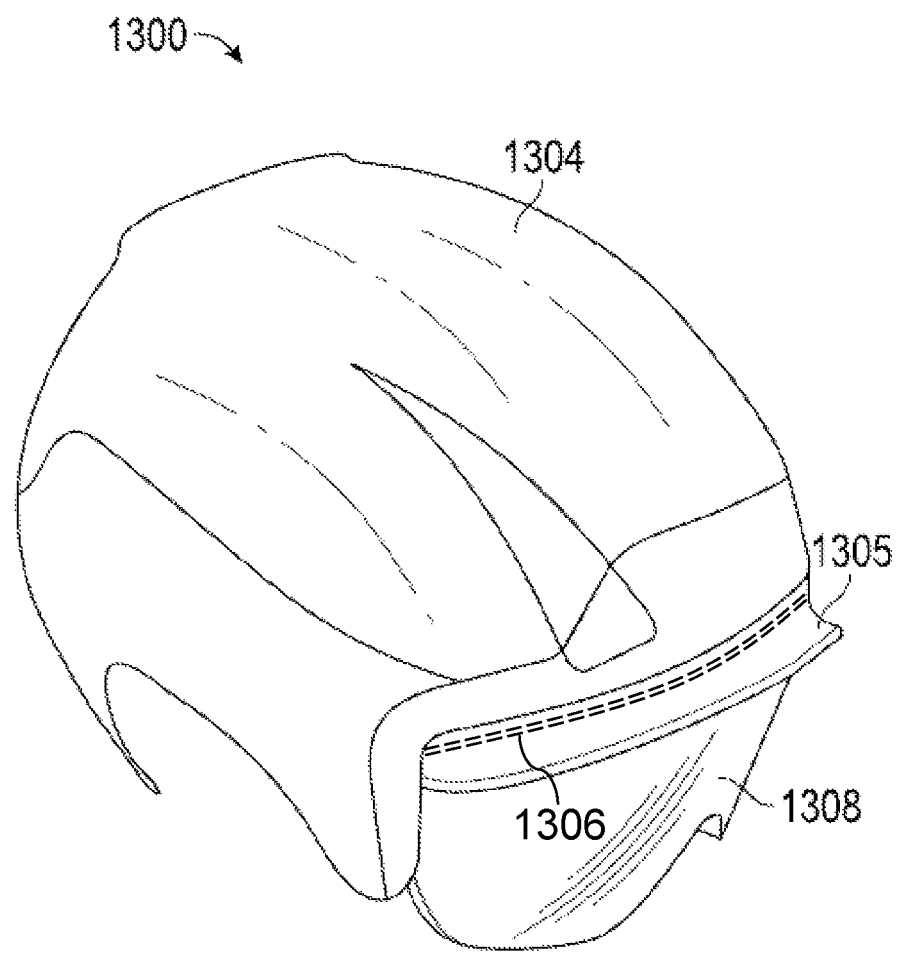
FIG. 13 illustrates a view of a helmet having a portion of a lens that is unsupported forming a gap between the lens and a brim of the helmet.

Any and all of the features described above with respect to embodiments and lenses, such as passive venting, passive retention mechanisms, and active retention mechanisms, may be used in other types of headworn supports including, but not limited to, helmets, face masks, balaclavas, and breaching shields. FIG. 13 illustrates a perspective view of an example helmet 1300 configured to be used with a lens 1308 and which incorporates the passive venting features described above. The helmet 1300 is configured to receive the lens 1308 within a support structure, such as a brow 1305 of a helmet frame 1304. The lens 1308 comprises an arcuate unitary lens which extends across both of the wearer's right and left eye fields of view. The lens 1308 is supported by the frame 1304 wherein the frame 1304 is configured to extend around at least an upper portion of the lens 1308 and configured to surround the head of a user. The lens 1308 is configured with a downwardly concave indent or nosepiece opening for receiving the nose. The inner surface of the frame 1304 can be covered with a compressible material, and is adapted to contact the wearer's head.

When worn, the surface of the compressible material disposed at the inner surface of the helmet 1300 makes contact with the wearer's head including the wearer's face. This wearer-contacting surface has a radius of curvature in the horizontal plane that is adapted to conform from side to side of the wearer's face.

A portion of the helmet frame 1304, such as a portion of the brow, such as a brim 1305, can include a pliable and flexible portion to allow the lens 1308 to be easily inserted and removed. The brow 1305 can include a groove 1306 around an interior portion of the brow 1305 to provide a guide for the lens 1308. The lens 1308 can be positioned within the groove 1306 structure, wherein the groove 1306 structure includes one or more features that act as passive retention mechanisms to secure the lens in place during use. The helmet frame 1304 can be worn on the head of the user without the lens 1308, if so desired.

Example Headworn Support Kits

In some instances, the lenses described herein can be interchangeably used with a variety of different bead worn supports each having a different structure and function including, but not limited to, helmets, face masks, balaclavas, breaching shields, and eyewear such as eyeglasses and goggles. For example, in some instances, the same lens can be interchangeably used with a helmet, goggles, and/or an eyeglass. A particular lens can be utilized with any other combination of two or more different headworn supports. This can beneficially allow the wearer to utilize a single lens with a variety of different headworn supports depending on the particular activity. For example, the wearer may utilize the lens with a cycling helmet when biking and switch the lens onto an eyeglass when off the bike. In some instances, the wearer may later switch the lens from the eyeglass and onto a snow helmet, goggle, or balaclava for skiing.

Figure 11A:
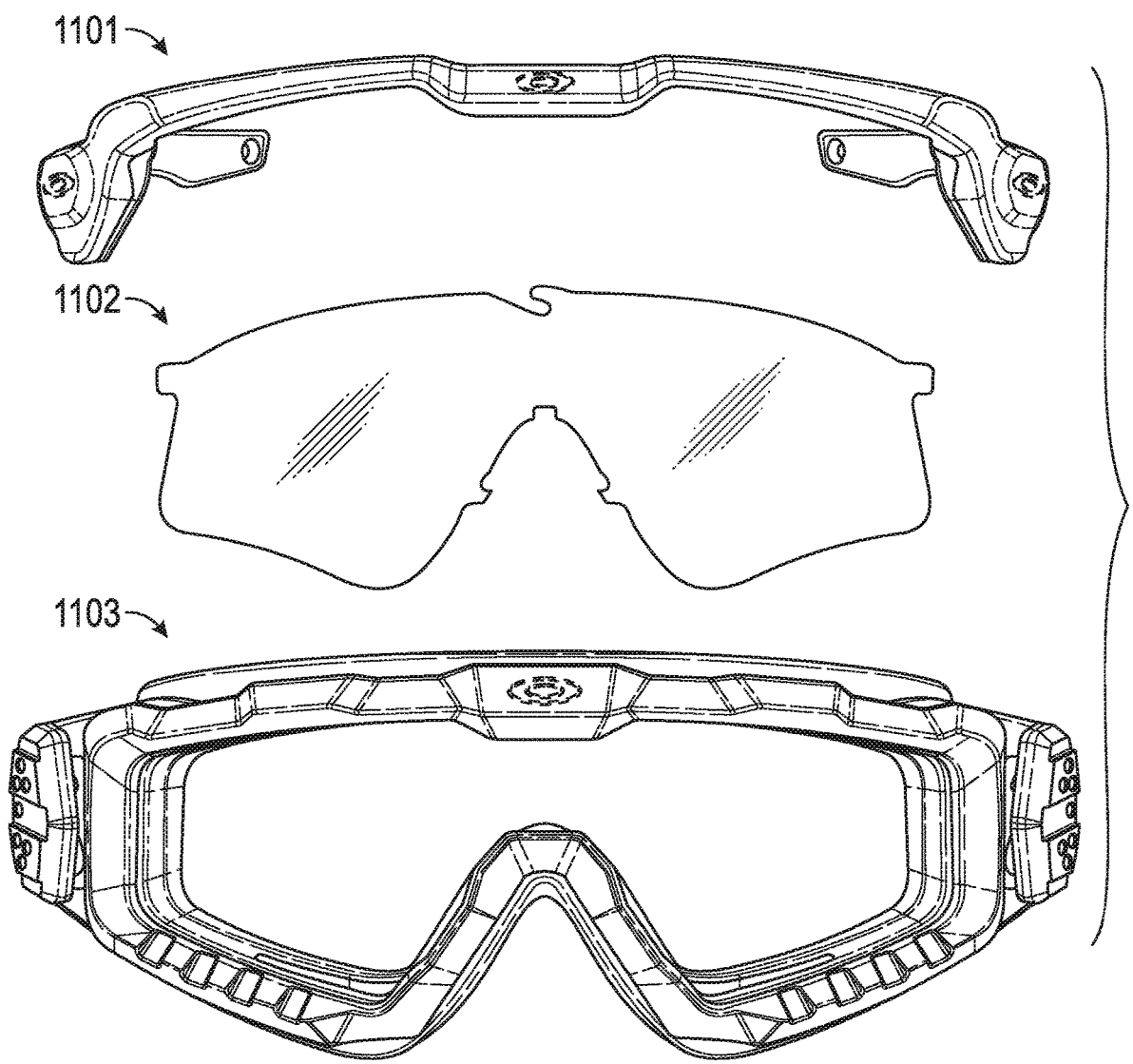
FIGS. 11A and 11B respectively illustrate front elevational and from perspective views of an example kit having an eyewear frame, a goggle frame, and a lens compatible with both the eyewear frame and the goggle frame.
Figure 11B:
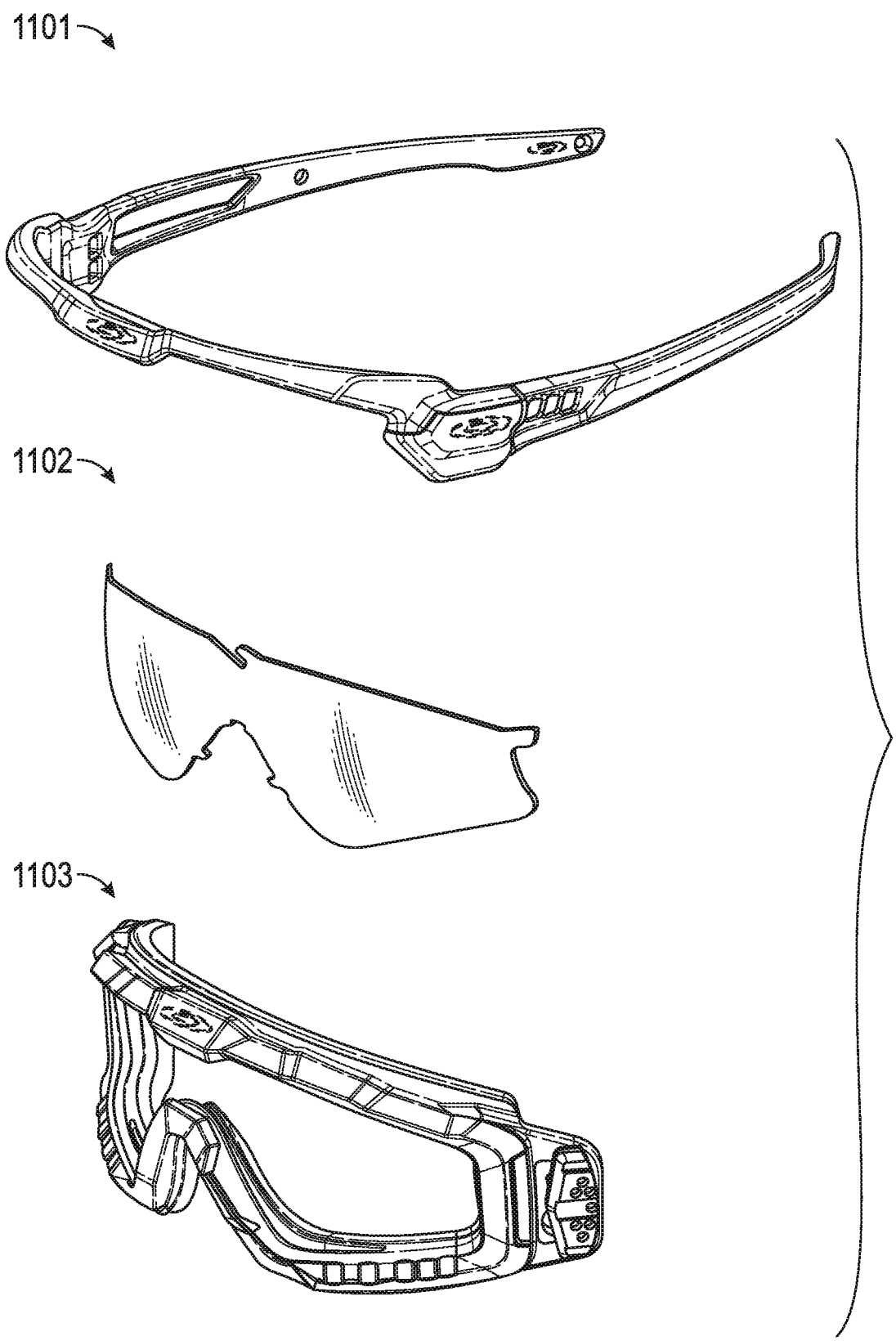
Figure 12A:
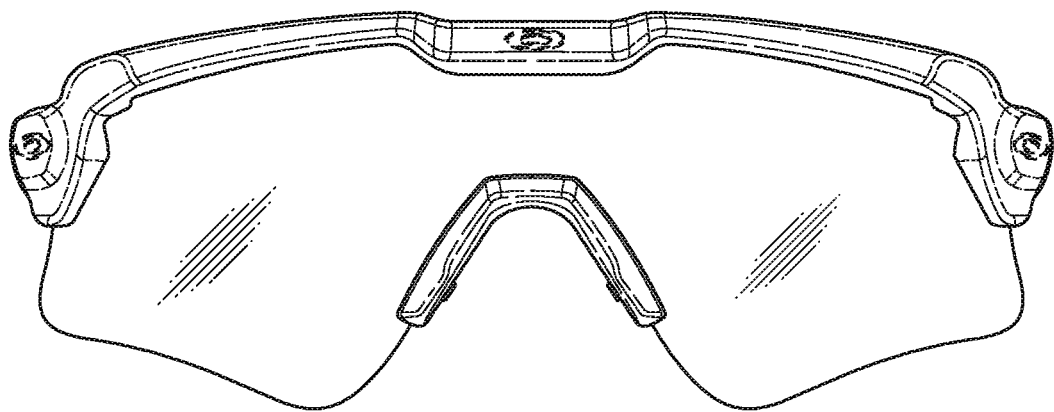
FIGS. 12A and 12B illustrate views of the example kit of FIGS. 11A and 11B assembled into an eyeglass and into a goggle.
Figure 12A:
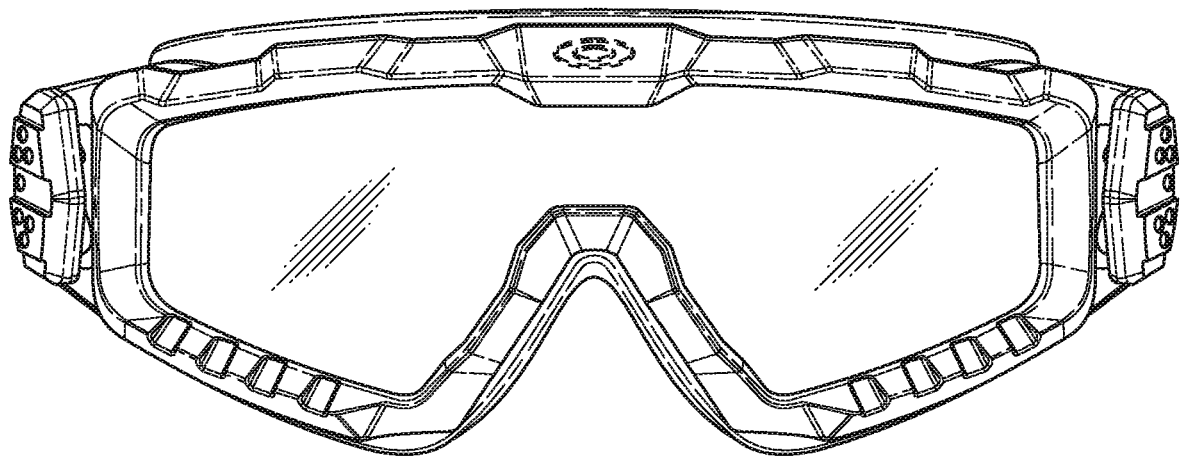
Figure 12B:
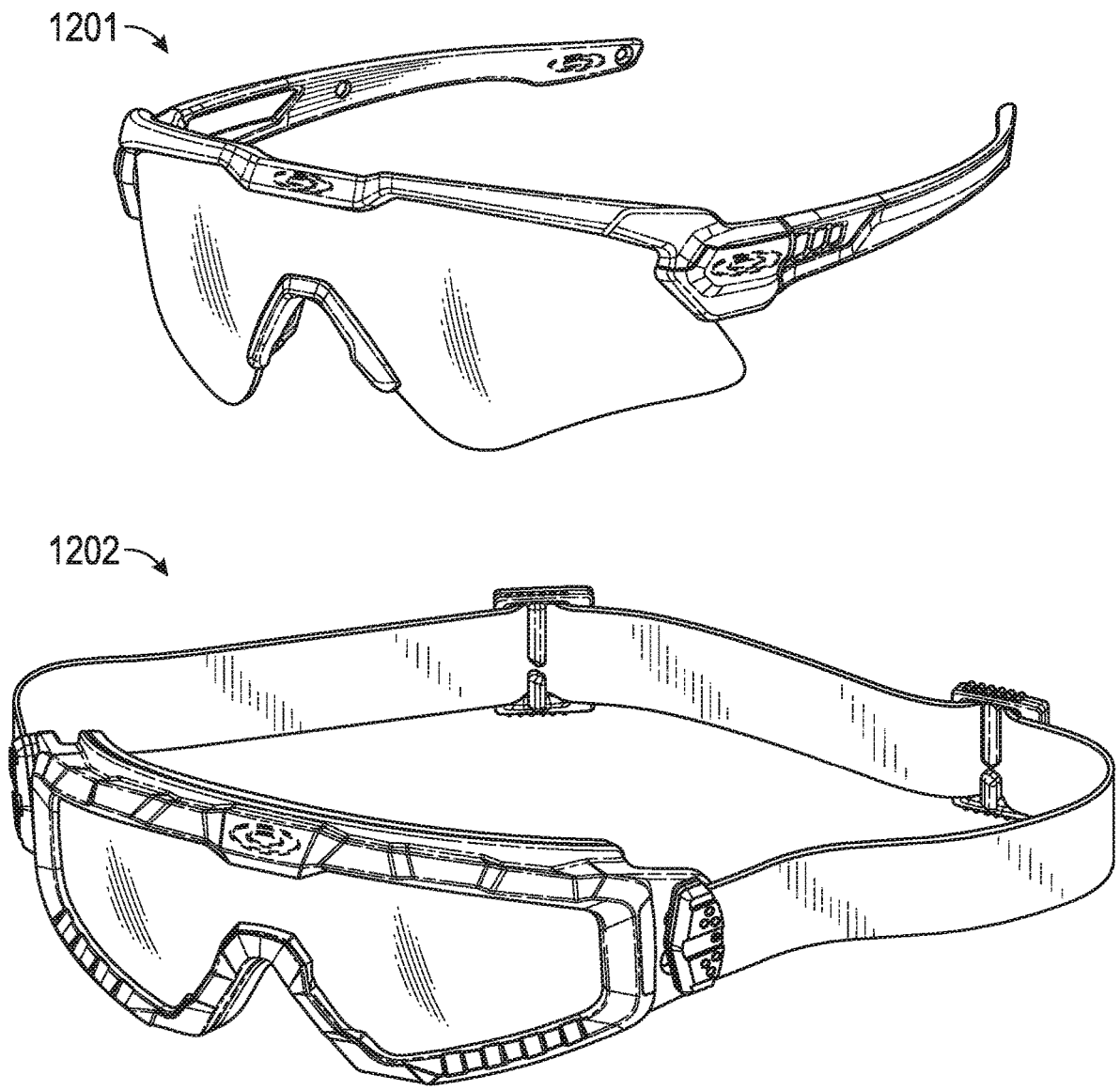

FIGS. 11A and 11B respectively illustrate front elevational and front perspective views of an example kit having an eyeglass frame 1101, a goggle frame 1103, and a lens 1102 compatible with both the eyeglass frame and the goggle frame. The lens 1102 can be a unitary lens, as illustrated, or it can be two or more lenses. As described herein, the same lens 1102 can be configured to be secured to the eyeglass frame 1101 and the goggle frame 1103 using complementary but different retention mechanisms. In some embodiments, each of the eyeglass frame 1101 and the goggle frame 1103 can be independently worn without the lens 1102. FIGS. 12A and 12B illustrate views of the example kit of FIGS. 11A and 11B assembled into an eyeglass 1201 and into a goggle 1202. In some embodiments, the eyeglass 1201 can be formed by securing the lens 1102 to the eyeglass frame 1101 and the goggle 1202 can be formed by securing the lens 1102 to the goggle frame 1103, wherein the eyeglass frame 1101 and the goggle frame 1103 do not share any components from the kit when forming the eyeglass 1201 and the goggle 1202. For example, to form the eyeglass 1201, the lens 1102 is secured to the eyeglass frame 1101. Then, to form the goggle 1202, the lens 1102 can be removed from the eyeglass frame 1101 and secured to the goggle frame 1103 without including any additional components from the eyeglass frame 1101 to form the goggle 1202. This same functionality can apply when forming the eyeglass 1201 after first forming the goggle 1202. This interchangeable lens 1102 allows for an eyeglass frame 1101 and a goggle frame 1103 to be purchased and to be able to replace the lenses of each with compatible lenses when the lenses break or when different functionality is desired. Thus, the kits can provide eyewear that does not need to be replaced when the lens no longer provides desired functionality. In addition, the kit provides eyewear with the passive venting functionality and ballistic performance described herein.

Example Ballistic Performance

Some embodiments of the eyewear described herein can provide desirable and advantageous passive venting functionality. In addition or in the alternative, the disclosed eyewear can provide increased lens stability and ballistic resistance. This may be due at least in part to the retention system implemented with the lens and frames. For example, by allowing a lower edge of the lens to float free from the frame, impact on the lens can cause the lens to deform and absorb the impact due at least in part to a tympanic response to the impact. This can allow the lens to deform rather than shatter, which may otherwise Ire the case if the lens were rigidly attached around the entirety of the perimeter of the lens. The gaps that provide the passive venting can also act to provide desirable ballistic performance.

Some embodiments of the eyeglass disclosed herein can help the lens to resist becoming transitorily and/or permanently substantially separated from the frame in response to a ballistic event. Some embodiments of the eyeglass can be configured such that a force transmitted to the lens is substantially entirely transmitted to the frame of the eyeglass while substantially maintaining engagement between the lens and the frame. For example, although the lens of such an eyeglass may be damaged (cracked or chipped), the lens avoids shattering or displacing relative to the frame. This ballistic resistance can provide excellent protection to the wearer.

In some embodiments, the goggles and eyeglasses described herein can be impact resistant. For example, the eyewear can be configured to resist ballistic impacts, for example, for combat uses. The frames can be configured to retain the lens in the event of an impact on the lens and to allow the lens to deform without shattering. The active retention mechanism can be configured to remain in the closed position in the event of an impact on the lens vine to the interaction with the earstem, as described hemin.

In some embodiments, the eyewear, such as eyeglasses described herein, can conform to the American National Standard for Occupational and Educational Personal Eye and Face Protection Devices standard ANSI/ISEA Z87.1-2010. For example, the eyewear can be configured to resist impact from a 6.35 mm (0.25 in.) diameter steel ball traveling at about 150 ft/s. In such a situation, the eyewear can be configured to prevent contact of the ball with the eye of a user. Similarly, the eyewear disclosed herein can conform to the Performance Specification for the Military Combat Eye Protection (MCEP) System standard MIL-PRT-32432(GL). For example, the eyewear can be configured to resist impact from a .15 caliber, 5.85 grain, T37 shaped projectile (e.g., a cylindrical-shaped, chamfered-edge fragment) at 640 to 660 ft/sec (e.g., about 650 ft/sec) at normal incidence to the primary lens without cracking, fracturing, or shattering, without being penetrated, or without having one or more fragments dislodging, etc.

Terminology

Conditional language used herein, such as, among others, "can," "could," "might," "may," "e.g.," and the like, unless specifically slated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z" unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. Any structure, feature, step, or process disclosed herein in one embodiment can be used separately or combined with or used instead of any other structure, feature, step, or process disclosed in any other embodiment. Also, no structure, feature, step, or processes disclosed herein is essential or indispensable; any may be omitted in some embodiments. The scope of certain embodiments disclosed herein is indicated by the appended claims rather than by the foregoing description. All changes which come within the meaning and range of equivalency of the claims are to be embraced within their scope.

The following is claimed:

1. A headworn support kit comprising:
    a lens comprising;
        a first lateral end portion and a second lateral end portion both lateral of a wearer's eyes in an as-worn position;
        a horizontal axis extending between the first and second lateral end portions;
        a first projection extending, at the first lateral end portion, along the horizontal axis in a first direction;
        a second projection extending, at the second lateral end portion, along the horizontal axis in a second direction opposite the first direction;
        a medial portion between the first and second lateral end portions of the lens;
        an angled projection extending, at the medial portion, diagonally with respect to the horizontal axis and forming a notch that extends diagonally with respect to the horizontal axis into an upper surface of the lens;
    a first frame comprising:
        a first lens support adapted to receive the lens,
        a movable projection to selectively secure the lens relative to the first frame, the movable projection being disposed at and movable relative to a first lateral end portion of the first lens support, the movable projection being lateral of the wearer's eyes in an as-worn position, and
        a first passive retention mechanism disposed at a second lateral end portion of the first lens support, the first passive retention mechanism being lateral of the wearer's eyes in an as-worn position and comprising a groove configured to receive the second projection of the lens, wherein the second lateral end portion of the first lens support is configured to support the lens solely with the first passive retention mechanism,
        a second passive retention mechanism disposed at a medial portion of the first lens support between the first and second lateral end portions of the first lens support, the second passive retention mechanism comprising a guide slot configured to receive the angled projection and align the first projection of the lens for securement to the first frame by the movable projection, wherein the medial portion of the first lens support is configured to support the lens solely with the second passive retention mechanism; and
    a second frame comprising:
        a second lens support adapted to support the lens in the wearer's field of view, the second lens support having a channel configured to receive the lens and secure the lens in place,
    wherein the lens is interchangeable between the first frame and the second frame such that the lens is configured to be removable from and supported by the first frame and the second frame.

2. The headworn support kit of claim 1, wherein:
    the first frame is an eyeglass frame and the first lens support is an eyeglass lens support, the eyeglass frame comprising an earstem attached to the eyeglass lens support; and
    the second frame is a goggle frame, the goggle frame comprising a padded layer attached to a posterior surface of the second lens support, the padded layer configured to be pressed against a head of the wearer when in use.

3. The headworn support kit of claim 1, wherein the lens comprises a unitary lens.

4. The headworn support kit of claim 3, wherein the first frame further comprises one or more contact points configured to contact the unitary lens when the lens is secured to the first frame.

5. The headworn support kit of claim 4, wherein, between two or more contact points, a posterior surface of the first frame extends a protrusion distance rearward beyond a posterior extension of a posterior surface of the lens, the protrusion distance being less than or equal to about 4 millimeters.

6. The headworn support kit of claim 5, wherein when the lens is secured to the first frame, an upper edge of the lens and a lower edge of the first lens support are spaced apart between two or more contact points to allow venting of the lens.

7. The headworn support kit of claim 6, wherein a total chord length of the upper edge that is spaced apart from the first frame is at least 20% of a total chord length of the upper edge of the lens.

8. The headworn support kit of claim 4, wherein, between two or more contact points, a posterior surface of the first frame extends a protrusion distance rearward beyond a posterior extension of a posterior surface of the lens, the protrusion distance being less than or equal to about 3.2 times a center thickness of the lens.

9. The headworn support kit of claim 8, wherein the protrusion distance is less than or equal to the center thickness of the lens.

10. The headworn support kit of claim 1, the first frame comprising a posterior surface facing toward the wearer's head in an as-worn position, wherein when the lens is secured to the first frame, at least one gap is formed between the posterior surface of the first frame and an anterior surface of the lens facing away from the wearer's head in an as-worn position, the at least one gap positioned at a region where the posterior surface of the first frame overlaps the anterior surface of the lens.

11. The headworn support kit of claim 1, wherein a headworn support comprising the lens secured to the first frame or the lens secured to the second frame is configured to withstand a ballistic impact of a 0.25" diameter steel ball having a speed of at least about 150 feet per second.

12. The headworn support kit of claim 1, wherein a headworn support comprising the lens secured to the first frame or the lens secured to the second frame is configured to withstand a ballistic impact of a 0.15 caliber, 5.85 grain, cylindrical-shaped, chamfered edge fragment having a speed of at least about 640 feet per second.

13. The headworn support kit of claim 1, wherein:
the first frame is an eyeglass frame and the first lens support is an eyeglass lens support, the eyeglass frame comprising an earstem attached to the eyeglass lens support; and
the second frame includes a portion of a helmet configured to be worn on the head of the wearer when in use.

14. The headworn support kit of claim 1, wherein the first lens support has a partial orbital, and wherein the second lens support has a full orbital.

15. The headworn support kit of claim 1, wherein the first frame is an eyewear frame and the second frame is a helmet frame.

16. The headworn support kit of claim 1, wherein:
the first frame comprises earstems, the first lens support having a partial orbital; and
the second frame comprises earstems, the second lens support having a full orbital.

17. The headworn support kit of claim 1, wherein
the movable projection comprises a door to selectively cover the first projection.

18. The headworn support kit of claim 17, the first frame further comprising an earstem pivotably attached to the first lens support, wherein pivoting the earstem from a folded position to an extended position relative to the first lens support closes the door over the protrusion first projection, thereby locking the lens to the first lens support.

19. The headworn support kit of claim 17, the first frame further comprising an earstem pivotably attached to the first lens support, wherein the earstem prevents the door from opening when the earstem is in an extended position relative to the first lens support.

20. The headworn support kit of claim 1, wherein the first frame and the second frame are structurally different.

21. A headworn support kit comprising:
a unitary lens comprising:
a lateral end portion lateral of a wearer's eyes in an as-worn position, and
a projection extending at the lateral end portion;
an eyewear frame comprising:
a locking receptacle;
an eyeglass lens support adapted to receive the unitary lens, an earstem attached to the eyeglass lens support, and an active retention mechanism to selectively secure the unitary lens relative to the eyewear frame, the active retention mechanism comprising a movable projection disposed at and rotatable relative to a lateral side of the eyeglass lens support, as defined in an as-worn orientation, between a first position in which the unitary lens is locked within the active retention mechanism and a second position in which the unitary lens is removable from the active retention mechanism, the movable projection comprising:
a door configured to cover the projection of the unitary lens in the first position; and
an engaging projection, coupled to the door, configured to be inserted, upon rotation of the movable projection to the first position, through the locking receptacle under the projection of the unitary lens to support the projection of the unitary lens; and
a goggle frame comprising:
a goggle lens support adapted to support the unitary lens in a wearer's field of view, the goggle lens support having a channel configured to receive the unitary lens and secure the unitary lens in place,
wherein the goggle frame comprises a padded layer attached to a posterior surface of the goggle lens support,
wherein the padded layer is configured to be pressed against a head of the wearer when in use, and
wherein the unitary lens is interchangeable between the eyewear frame and the goggle frame such that the unitary lens is configured to be removable from and supported by the eyewear frame and the goggle frame.

22. The headworn support kit of claim 21, wherein the eyewear frame further comprises one or more contact points configured to contact the unitary lens when the unitary lens is secured to the eyewear frame.

23. The headworn support kit of claim 22, wherein, between two or more contact points, a posterior surface of the eyewear frame extends a protrusion distance rearward beyond a posterior extension of a posterior surface of the unitary lens, the protrusion distance being less than or equal to about 4 mm.

24. The headworn support kit of claim 23, wherein when the unitary lens is secured to the eyewear frame, an upper edge of the unitary lens and a lower edge of the eyeglass lens support are spaced apart between two or more contact points to allow venting of the unitary lens, and
wherein a total chord length of the upper edge that is spaced apart from the frame is at least 20% of a total chord length of the upper edge of the unitary lens.

25. The headworn support kit of claim 21, the eyewear frame comprising a posterior surface facing toward the head of the wearer in an as-worn position, wherein when the unitary lens is secured to the eyewear frame, at least one gap is formed between the posterior surface of the eyewear frame and an anterior surface of the unitary lens facing away from the head of the wearer in an as-worn position, the at least one gap positioned at a region where the posterior surface of the eyewear frame overlaps the anterior surface of the unitary lens.

26. The headworn support kit of claim 21, wherein the unitary lens comprises lateral and medial engagement sections, and
wherein the channel secures the unitary lens in place via the lateral and medial engagement sections.

27. The headworn support kit of claim 21, wherein the eyewear frame further comprises a passive retention mechanism disposed on a medial side of the eyeglass lens support and stationary with respect to the eyeglass lens support, the passive retention mechanism comprising at least one of a recess, a surface contour, a cutout, a projection, a slot, or an aperture to retain the unitary lens.

28. A headworn support kit comprising:
a unitary lens;
an eyewear frame comprising:
a first lens support adapted to receive the unitary lens, the eyewear frame configured to receive the unitary lens within the first lens support; and
a posterior surface facing toward a wearer's head in an as-worn position, wherein when the unitary lens is secured to the eyewear frame, at least one gap is formed between the posterior surface of the eyewear frame and an anterior surface of the unitary lens facing away from the wearer's head in an as-worn position, the at least one gap positioned at a region where the posterior surface of the eyewear frame overlaps the anterior surface of the unitary lens;
a goggle frame comprising:
a second lens support, the goggle frame configured to receive the unitary lens within the second lens support, the second lens support having a channel configured to receive the unitary lens and secure the unitary lens in place; and a third frame comprising:
a third lens support, the third frame configured to receive the unitary lens within the third lens support, the third lens support having a groove configured to receive the unitary lens and secure the unitary lens in place,
wherein the unitary lens is interchangeable between the eyewear frame, the goggle frame, and the third frame such that the unitary lens is configured to be removable from and supported by the eyewear frame, the goggle frame, and the third frame,
wherein the eyewear frame, the goggle frame, and the third frame are structurally different,
wherein the first lens support, the second lens support, and the third lens support are each structurally different from one another, and
wherein the eyewear frame, the goggle frame, and the third frame do not share any components of the eyewear frame, the goggle frame, or the third frame, such that the unitary lens is securable to any one of the frames without including any of the components of another of the frames.

29. The headworn support kit of claim 28, wherein the third frame is a helmet frame.

30. The headworn support kit of claim 28, wherein the unitary lens comprises a protrusion extending from a boundary of the unitary lens, and
wherein the first lens support is configured to receive the protrusion of the unitary lens.

31. The headworn support kit of claim 28, wherein the eyewear frame comprises earstems, the first lens support of the eyewear frame having a partial orbital, and wherein the third frame comprises earstems, the third lens support of the third frame having a full orbital.

32. The headworn support kit of claim 28, the eyewear frame comprising:
a movable projection to selectively secure the unitary lens relative to the eyewear frame, the movable projection being disposed at and movable relative to a first lateral end portion of the first lens support, the movable projection being lateral of a wearer's eyes in an as-worn position, and
a passive retention mechanism disposed at a second lateral end portion of the first lens support, the passive retention mechanism being lateral of the wearer's eyes in an as-worn position, wherein the second lateral end portion is configured to support the unitary lens solely with the passive retention mechanism.

33. The headworn support kit of claim 28, the eyewear frame comprising a single active retention mechanism to selectively secure the unitary lens relative to the eyewear frame, the single active retention mechanism comprising a movable projection disposed at and movable relative to a lateral side of the first lens support, as defined in an as-worn orientation, between a first position in which the unitary lens is locked within the single active retention mechanism and a second position in which the unitary lens is removable from the single active retention mechanism.

* * * * *

UNITED STATES PATENT AND TRADEMARK OFFICE
CERTIFICATE OF CORRECTION

| | |
|---|---|
| PATENT NO. | : 12,239,579 B2 |
| APPLICATION NO. | : 16/708140 |
| DATED | : March 4, 2025 |
| INVENTOR(S) | : Calilung et al. |

It is certified that error appears in the above-identified patent and that said Letters Patent is hereby corrected as shown below:

On the Title Page

Column 2, item (57), in "ABSTRACT", Line 1, delete "bead worn" and insert -- headworn --, therefor.

Column 2, item (57), in "ABSTRACT", Line 8, delete "hemin" and insert -- herein --, therefor.

In the Specification

In Column 1, Line 25, delete "head wont" and insert -- headworn --, therefor.

In Column 2, Line 21, delete "limes" and insert -- times --, therefor.

In Column 2, Line 25, delete "docs" and insert -- does --, therefor.

In Column 2, Line 31, delete "titan" and insert -- than --, therefor.

In Column 2, Line 34, delete "al" and insert -- at --, therefor.

In Column 3, Line 17, delete "tin" and insert -- an --, therefor.

In Column 3, Line 31, delete "mote" and insert -- more --, therefor.

In Column 3, Line 35, delete "ex tends" and insert -- extends --, therefor.

In Column 3, Line 43, delete "al" and insert -- at --, therefor.

In Column 4, Lines 10-11, delete "re used" and insert -- re-used --, therefor.

In Column 4, Line 24, delete "lop" and insert -- top --, therefor.

Signed and Sealed this
Twenty-fourth Day of June, 2025

Coke Morgan Stewart
*Acting Director of the United States Patent and Trademark Office*

In Column 4, Line 44, delete "from" and insert -- front --, therefor.

In Column 4, Line 66, delete "head worn" and insert -- headworn --, therefor.

In Column 5, Line 25, delete "head worn" and insert -- headworn --, therefor

In Column 5, Line 28, delete "eye wear)" and insert -- eyewear) --, therefor.

In Column 5, Line 33, delete "wearers" and insert -- wearer's --, therefor.

In Column 5, Line 35, delete "head worn" and insert -- headworn --, therefor.

In Column 6, Line 13, delete "head worn" and insert -- headworn --, therefor.

In Column 6, Line 34, delete "al" and insert -- at --, therefor.

In Column 6, Line 38, delete "al" and insert -- at --, therefor.

In Column 6, Line 66, delete "using, a bead" and insert -- using a head --, therefor.

In Column 7, Line 6, delete "108a." and insert -- 108a, --, therefor.

In Column 7, Line 36, delete "nest" and insert -- rest --, therefor.

In Column 7, Line 37, delete "108a." and insert -- 108a, --, therefor.

In Column 7, Line 41, delete "108a." and insert -- 108a, --, therefor.

In Column 7, Line 45, delete "108a." and insert -- 108a, --, therefor.

In Column 7, Line 48, delete "off set" and insert -- offset --, therefor.

In Column 7, Line 53, delete "108a." and insert -- 108a, --, therefor.

In Column 7, Line 63, delete "108a." and insert -- 108a, --, therefor.

In Column 8, Line 16, delete "general" and insert -- general, --, therefor.

In Column 8, Line 21, delete "108a." and insert -- 108a, --, therefor.

In Column 8, Line 25, delete "108a." and insert -- 108a, --, therefor.

In Column 8, Line 31, delete "108a." and insert -- 108a, --, therefor.

In Column 8, Line 34, delete "108a." and insert -- 108a, --, therefor.

CERTIFICATE OF CORRECTION (continued)
U.S. Pat. No. 12,239,579 B2

In Column 8, Line 45, delete "108a." and insert -- 108a, --, therefor.

In Column 8, Line 60, delete "KB" and insert -- 108 --, therefor.

In Column 9, Line 14, delete "KM" and insert -- 104 --, therefor.

In Column 9, Line 14, delete "KB" and insert -- 108 --, therefor.

In Column 9, Line 22, delete "KM" and insert -- 104 --, therefor.

In Column 9, Line 28, delete "tens" and insert -- lens --, therefor.

In Column 9, Line 50, delete "108a." and insert -- 108a, --, therefor.

In Column 9, Line 52, delete "(low" and insert -- flow --, therefor.

In Column 9, Line 58, delete "slated" and insert -- stated --, therefor.

In Column 9, Line 60, delete "108a." and insert -- 108a, --, therefor.

In Column 10, Line 2, delete "108a." and insert -- 108a, --, therefor.

In Column 10, Line 14, delete "surf ace" and insert -- surface --, therefor.

In Column 10, Line 17, delete "hieing" and insert -- facing --, therefor.

In Column 10, Line 53, delete "208a. 208b." and insert -- 208a, 208b, --, therefor.

In Column 11, Line 16, delete "508" and insert -- 108 --, therefor.

In Column 11, Line 41, delete "sealed" and insert -- seated --, therefor.

In Column 11, Line 49, delete "cutouts," and insert -- cut-outs, --, therefor.

In Column 11, Line 54, delete "106a. 106b." and insert -- 106a, 106b, --, therefor.

In Column 11, Line 56, delete "106a. 106b." and insert -- 106a, 106b, --, therefor.

In Column 12, Line 12, delete "106a." and insert -- 106a, --, therefor.

In Column 12, Line 45, delete "309a." and insert -- 309a, --, therefor.

In Column 12, Line 62, delete "309a." and insert -- 309a, --, therefor.

In Column 12, Line 63, delete "al" and insert -- at --, therefor.

In Column 12, Line 64, delete "al" and insert -- at --, therefor.

In Column 13, Line 7, delete "425" and insert -- 42.5 --, therefor.

In Column 13, Line 18, delete "al" and insert -- at --, therefor.

In Column 13, Line 22, delete "57.5" and insert -- 17.5 --, therefor.

In Column 13, Line 37, delete "309a." and insert -- 309a, --, therefor.

In Column 13, Line 45, delete "309a." and insert -- 309a, --, therefor.

In Column 13, Line 49, delete "309a." and insert -- 309a, --, therefor.

In Column 13, Line 56, delete "309a." and insert -- 309a, --, therefor.

In Column 14, Line 36, delete "0.3" and insert -- 3 --, therefor.

In Column 15, Line 19, delete "al" and insert -- at --, therefor.

In Column 15, Line 55, delete "2, mm" and insert -- 2 mm, --, therefor.

In Column 15, Line 56, delete "12 mm" and insert -- 1.2 mm. --, therefor.

In Column 15, Line 64, delete "al" and insert -- at --, therefor.

In Column 15, Line 64, delete "degrees, in" and insert -- degrees. In --, therefor.

In Column 16, Line 13, delete "mid" and insert -- and --, therefor.

In Column 16, Line 36, delete "heroin" and insert -- herein --, therefor.

In Column 16, Line 64, delete "sealed" and insert -- seated --, therefor.

In Column 17, Line 2, delete "near" and insert -- rear --, therefor.

In Column 17, Line 28, delete "entirely" and insert -- entirety --, therefor.

In Column 17, Line 30, delete "heroin," and insert -- herein, --, therefor.

In Column 17, Line 35, delete "entirely" and insert -- entirety --, therefor.

In Column 18, Line 5, delete "bead." and insert -- head. --, therefor.

In Column 18, Line 29, delete "cress-sectional" and insert -- cross-sectional --, therefor.

In Column 18, Line 51, delete "us" and insert -- as --, therefor.

In Column 18, Line 61, delete "309." and insert -- 309, --, therefor.

In Column 19, Line 36, delete "bead worn" and insert -- headworn --, therefor.

In Column 20, Line 31, delete "Ire" and insert -- be --, therefor.

In Column 20, Line 54, delete "vine" and insert -- due --, therefor.

In Column 20, Line 55, delete "hemin." and insert -- herein. --, therefor.

In Column 20, Line 66, delete "MIL-PRT-" and insert -- MIL-PRF- --, therefor.

In Column 21, Line 10, delete "slated" and insert -- stated --, therefor.

In the Claims

In Column 23, Claim 18, Line 59, after "over the" delete "protrusion".

In Column 25, Claim 28, Line 36, move "a third frame comprising" to a new paragraph (indentation of new paragraph matching that of Column 25, Line 31).